(12) United States Patent
Lombardo et al.

(10) Patent No.: US 8,388,685 B2
(45) Date of Patent: Mar. 5, 2013

(54) ARTIFICIAL INTERVERTEBRAL DISC

(75) Inventors: Alan Lombardo, Kinnelon, NJ (US);
Mark Semler, Morris Plains, NJ (US);
Joseph F. Ferraro, Londonderry, NH
(US); Theodore Karwoski, Hollis, NH
(US); Thomas M. Swanick,
Hillsborough, NH (US); **Brian C.
Sunter**, Londonderry, NH (US)

(73) Assignee: Blackstone Medical, Inc., Lewisville, TX (US)

( * ) Notice: Subject to any disclaimer, the term of this patent is extended or adjusted under 35 U.S.C. 154(b) by 753 days.

(21) Appl. No.: 11/534,313

(22) Filed: Sep. 22, 2006

(65) Prior Publication Data

US 2007/0073403 A1    Mar. 29, 2007

Related U.S. Application Data

(60) Provisional application No. 60/719,424, filed on Sep. 22, 2005, provisional application No. 60/759,944, filed on Jan. 18, 2006, provisional application No. 60/772,812, filed on Feb. 13, 2006, provisional application No. 60/745,303, filed on Apr. 21, 2006.

(51) Int. Cl.
*A61F 2/44* (2006.01)

(52) U.S. Cl. ..................................... 623/17.14

(58) Field of Classification Search ..... 623/17.11–17.16
See application file for complete search history.

(56) References Cited

U.S. PATENT DOCUMENTS

| | | | |
|---|---|---|---|
| 3,867,728 A | 2/1975 | Stubstad | |
| 4,820,305 A | 4/1989 | Harms et al. | |
| 6,375,682 B1 * | 4/2002 | Fleischmann et al. | 623/17.12 |
| 6,579,320 B1 * | 6/2003 | Gauchet et al. | 623/17.15 |
| 6,582,466 B1 * | 6/2003 | Gauchet | 623/17.11 |
| 6,626,943 B2 * | 9/2003 | Eberlein et al. | 623/17.15 |
| 6,645,248 B2 * | 11/2003 | Casutt | 623/17.12 |
| 6,726,721 B2 * | 4/2004 | Stoy et al. | 623/17.16 |
| 6,733,532 B1 * | 5/2004 | Gauchet et al. | 623/17.12 |
| 7,563,286 B2 * | 7/2009 | Gerber et al. | 623/17.14 |
| 7,641,692 B2 | 1/2010 | Bryan et al. | |
| 8,092,542 B2 | 1/2012 | Bryan et al. | |
| 2002/0035400 A1 * | 3/2002 | Bryan et al. | 623/17.15 |
| 2004/0093087 A1 | 5/2004 | Ferree et al. | |
| 2004/0117021 A1 * | 6/2004 | Biedermann et al. | 623/17.15 |
| 2004/0267369 A1 | 12/2004 | Lyons et al. | |
| 2005/0071007 A1 * | 3/2005 | Malek | 623/17.11 |
| 2005/0197702 A1 | 9/2005 | Coppes et al. | |
| 2006/0015183 A1 * | 1/2006 | Gilbert et al. | 623/17.11 |
| 2011/0295374 A1 | 12/2011 | Bryan et al. | |

FOREIGN PATENT DOCUMENTS

| JP | 05277141 | 10/1993 |
|---|---|---|
| JP | 2004505668 A | 2/2004 |

OTHER PUBLICATIONS

International Search Report and Written Opinion, International Application No. PCT/US06/37097, dated May 16, 2007, (7 pages).
Australian Office Action, AU Application No. 2006295462, dated Oct. 12, 2009, 2 pages.
Japanese Office Action, JP Application No. 2008-532443, dated Feb. 9, 2010, 8 pages.

* cited by examiner

*Primary Examiner* — Thomas Barrett
*Assistant Examiner* — Matthew Lawson
(74) *Attorney, Agent, or Firm* — Baker & McKenzie LLP

(57) ABSTRACT

The present invention is directed to the field of prosthetic devices. More particularly, one embodiment of the present invention is directed to an artificial disc that can be used as a replacement for an intervertebral disc (e.g., a human intervertebral lumbar disc, a human intervertebral cervical disc and/or a human intervertebral thoracic disc).

31 Claims, 45 Drawing Sheets

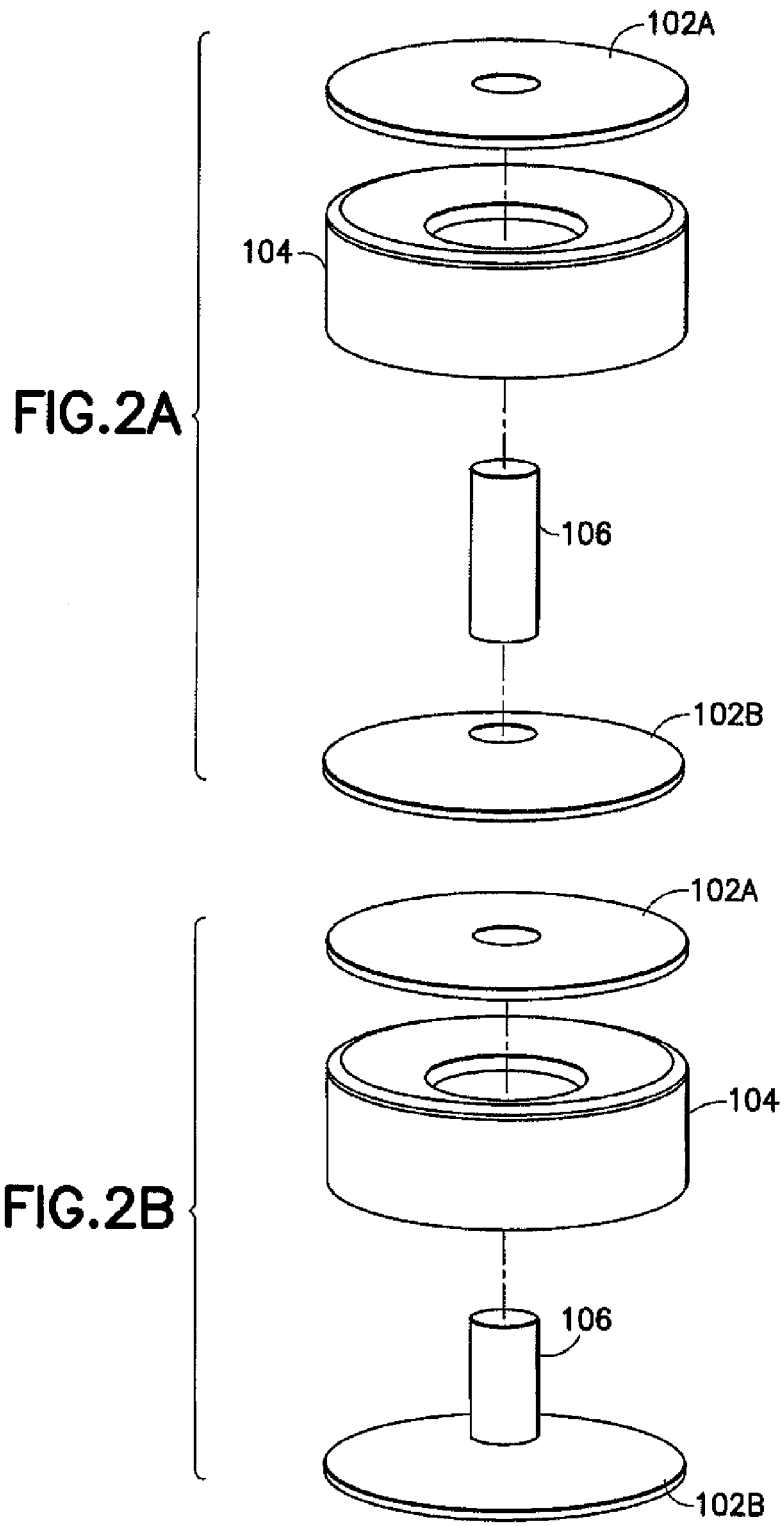

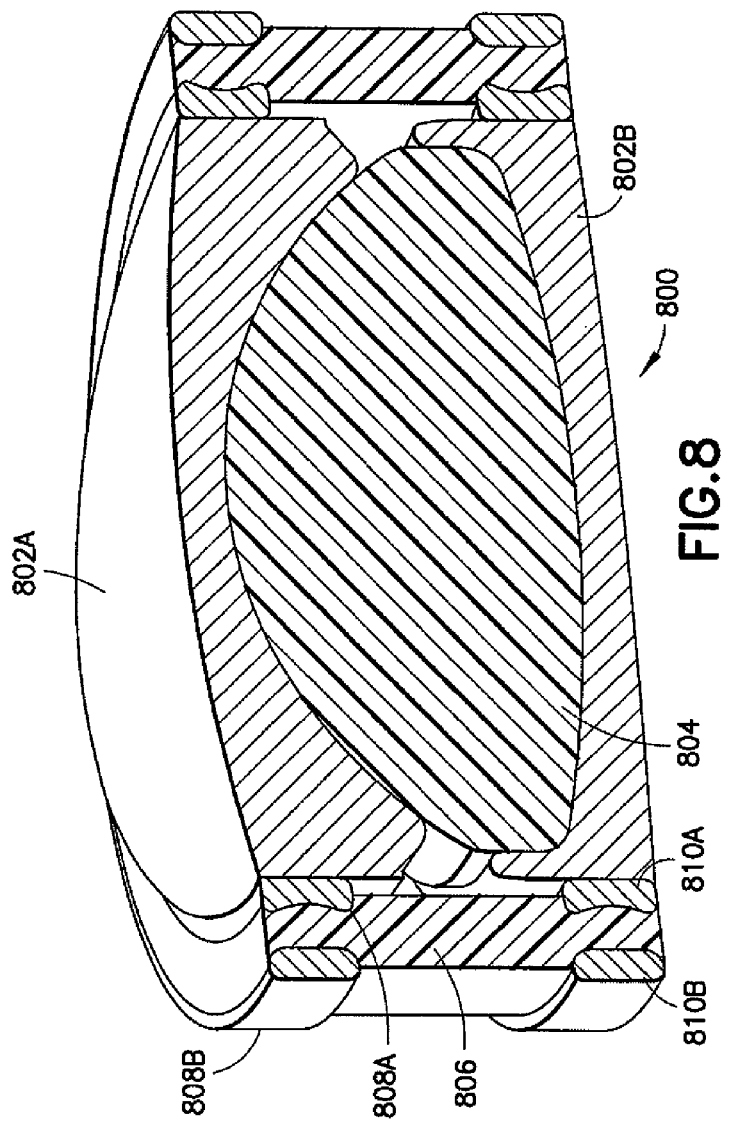

ARTIFICIAL INTERVERTEBRAL DISC

RELATED APPLICATIONS

This application claims the benefit of U.S. Provisional Application Ser. No. 60/719,424, filed Sep. 22, 2005, U.S. Provisional Application Ser. No. 60/759,944, filed Jan. 18, 2006, U.S. Provisional Application Ser. No. 60/772,812, filed Feb. 13, 2006 and U.S. Provisional Application Ser. No. 60/745,303, filed Apr. 21, 2006. Each of the aforementioned applications is incorporated herein by reference in its entirety.

FIELD OF THE INVENTION

The present invention is directed to the field of prosthetic devices. More particularly, one embodiment of the present invention is directed to an artificial disc that can be used as a replacement for an intervertebral disc (e.g., a human intervertebral lumbar disc, a human intervertebral cervical disc and/or a human intervertebral thoracic disc).

For the purposes of the present application the term "column" is intended to refer to a solid, partially hollow or hollow structure having any desired aspect ratio and any desired cross-section (cross-sectional shape and/or cross-sectional area). In one example (which example is intended to be illustrative and not restrictive) such a column may have a high length to width aspect ratio (i.e., the column may be "elongated"). In another example (which example is intended to be illustrative and not restrictive) such a column may have a low length to width aspect ratio (i.e., the column may be "squat"). In another example (which example is intended to be illustrative and not restrictive) the walls of the column may be thick enough to provide a substantial degree of inflexibility to the column. In another example (which example is intended to be illustrative and not restrictive) the walls of the column may be thin enough to provide a substantial degree of flexibility to the column. In other examples (which examples are intended to be illustrative and not restrictive) such a column may have a cross-section which is circular, oval, square or "kidney-shaped".

Further, for the purposes of the present application the term "filler" (e.g., as in column filler) is intended to refer to a substance disposed within a space or void which partially or fully fills the volume of the space or void.

Further still, for the purposes of the present application the term "composite structure" is intended to refer to a hollow or partially hollow column including a filler disposed therein.

Further still, for the purposes of the present application the term "elastomer" is intended to include (but not be limited to): a silicone, a urethane, a PCV, a thermoplastic elastomer, an elastomer alloy; a polyurethane/polycarbonate alloy, and/or any combination thereof Further still, for the purposes of the present application the term "biologically acceptable metal" is intended to include (but not be limited to): Ti, cobalt chromium, surgical steel and/or any combination thereof.

BACKGROUND OF THE INVENTION

As an alternative to spinal fusion techniques, numerous attempts have been made to design an artificial disc to replace, for example, an intervertebral lumbar disc that has become damaged or otherwise unhealthy.

BRIEF DESCRIPTION OF THE DRAWINGS

FIGS. 2A-2D show example assembly steps associated with the artificial intervertebral disc of FIG. 1;

FIG. 8 shows a cut-away view of an artificial intervertebral disc according to another embodiment of the present invention;

Figure 1:
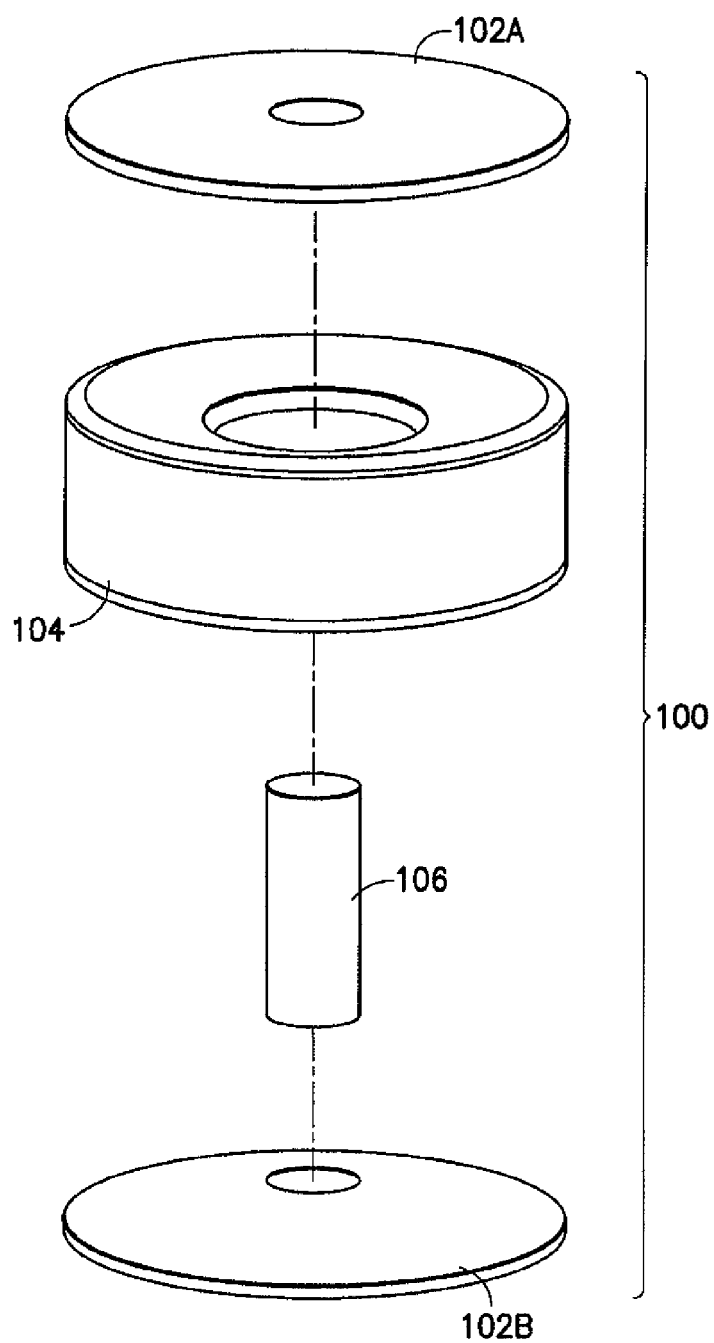
FIG. 1 shows an exploded view of an artificial intervertebral disc according to an embodiment of the present invention.
Figure 2C:
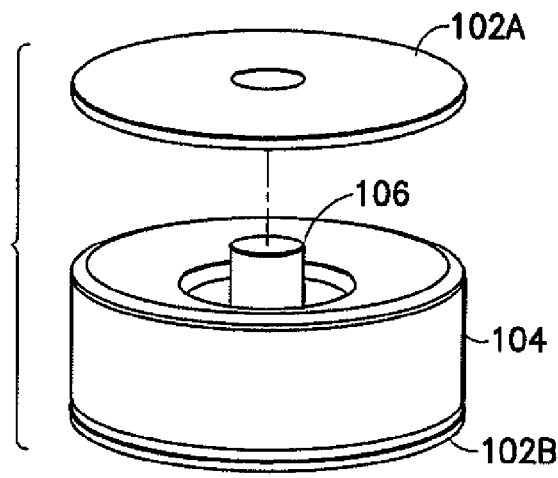
Figure 2D:
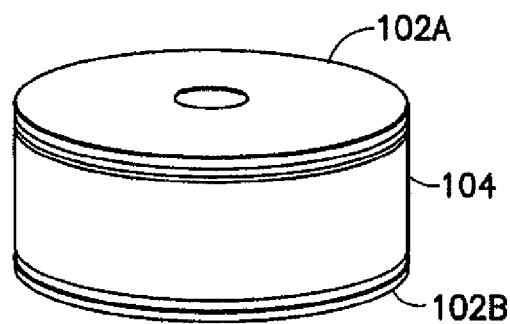

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

One embodiment of the present invention provides an artificial intervertebral disc ("AID") assembly comprised of first and second anchor plates (each of which has a vertebrae contacting side) and at least one composite structure that is fixed to the first and second anchor plates. The composite structure may be comprised of a column including woven and/or non-woven fiber(s). In one example (which example is intended to be illustrative and not restrictive), the column may comprise polyester. In a more specific example (which example is intended to be illustrative and not restrictive), the column may comprise DACRON. The column may be at least partially hollow (e.g., having one or more holes therein) and may be filled (fully or partially) with a compressible material, such as an elastomer. For example (which example is intended to be illustrative and not restrictive), the elastomer may include a silicone, a urethane, a thermoplastic elastomer, an elastomer alloy; a polyurethane/polycarbonate alloy, and/or any combination thereof.

Of note, the column filler (e.g., elastomer) may store energy and then return the stored energy back to the physiological system (because the column filler may allow physiological-like displacement, the column filler may (like a physiological system) dissipate some strain energy).

In one example (which example is intended to be illustrative and not restrictive), the compressive properties of the artificial intervertebral disc may be tuned to largely match those found in a natural intervertebral disc by utilizing a generally parabolic function. In a specific example applicable to a cervical disc (when deflection is plotted on the x-axis and compressive load is plotted on the y-axis), the parabola generally may be described by the function $y = A\ x^2 + B\ x + C$, where the coefficient A is in the range of 700 to 2000, the coefficient B is in the range of 0 to 1500, and the coefficient C is in the range 0 to 100 (the increasing stiffness is indicated by the increasing slope of the load-deflection curve at higher loads and deflections).

Referring now to FIG. 1 (showing one embodiment of the present invention), it is seen that Artificial Intervertebral Disc 100 includes First Anchor Plate 102A and Second Anchor Plate 102B (each Anchor Plate 102A, 102B may comprise, for example (which example is intended to be illustrative and not restrictive), any desired biologically acceptable metal). Of note, each Anchor Plate 102A, 102B may have an outer surface configured to be disposed adjacent a respective vertebral endplate (not shown). Further, Core 104 (e.g., comprising an elastomer) is sandwiched between an inner surface of Anchor Plate 102A and an inner surface of Anchor Plate 102B (in one example (which example is intended to be illustrative and not restrictive), the inner surfaces of Anchor Plates 102A, 102B may be convex and may be received in respective concavities in Core 104). In addition, Cable 106 (e.g., comprising a polymer and/or a metallic material (e.g., including a biologically acceptable metal)) is attached at a first end to Anchor Plate 102A and at a second end to Anchor Plate 102B (wherein Cable 106 runs from Anchor Plate 102A to Anchor Plate 102B through a hole disposed in Core 104).

In one example (which example is intended to be illustrative and not restrictive), Cable 106 may be attached to Anchor Plate 102A at a depression formed in an inner surface of Anchor Plate 102A and Cable 106 may be attached to Anchor Plate 102B at a depression formed in an inner surface of Anchor Plate 102B. In another example (which example is intended to be illustrative and not restrictive), Cable 106 may be attached to Anchor Plate 102A via a hole formed all the way through Anchor Plate 102A (i.e., a hole extending from an inner surface of Anchor Plate 102A to an outer surface of Anchor Plate 102A) and Cable 106 may be attached to Anchor Plate 102B via a hole formed all the way through Anchor Plate 102B (i.e., a hole extending from an inner surface of Anchor Plate 102B to an outer surface of Anchor Plate 102B). In another example (which example is intended to be illustrative and not restrictive), Cable 106 may be attached to Anchor Plates 102A, 102B using any appropriate attachment mechanism (e.g., adhesive, welding, screw(s), bolt(s), friction fitting(s), etc.).

Referring now to FIGS. 2A-2D, example assembly steps (which examples are intended to be illustrative and not restrictive) associated with the artificial intervertebral disc of FIG. 1 are shown.

Figure 3:
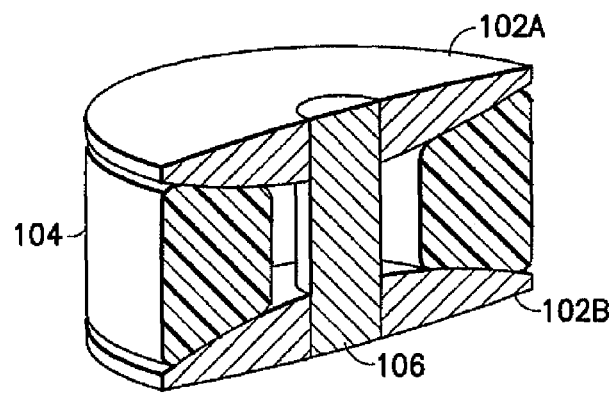
FIG. 3 shows a cut-away view of the assembled artificial intervertebral disc of FIG. 1.

Referring now to FIG. 3, a cut-away view of the assembled artificial intervertebral disc of FIG. 1 is shown.

Figure 4:
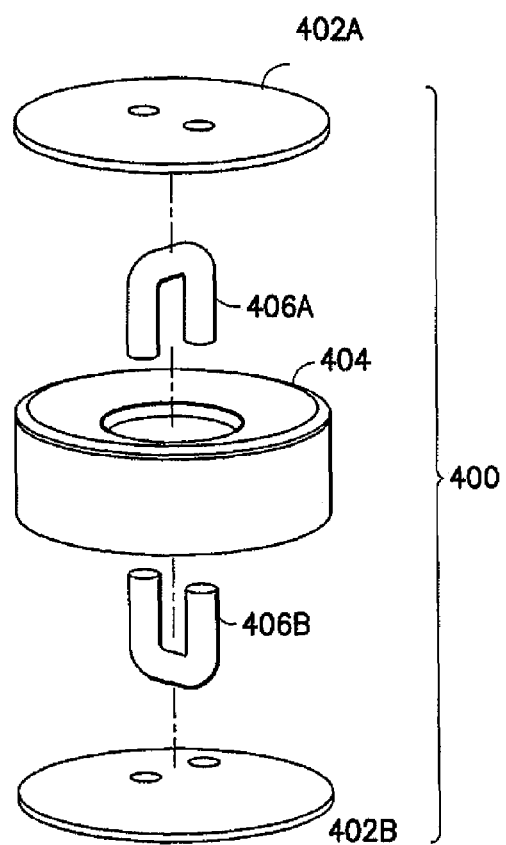
FIG. 4 shows an exploded view of an artificial intervertebral disc according to another embodiment of the present invention.
Figure 5A:
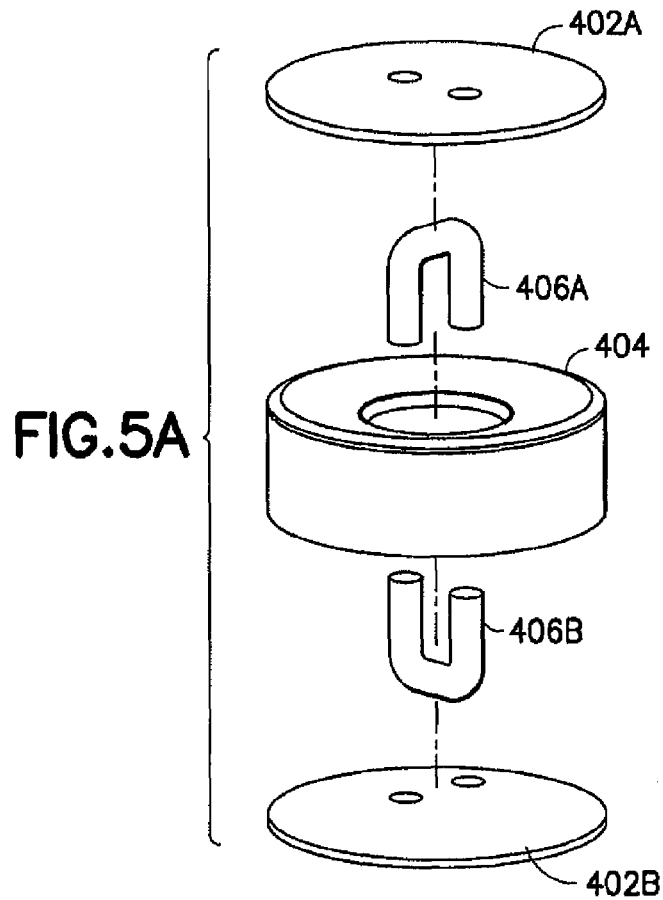
FIGS. 5A-5D show example assembly steps associated with the artificial intervertebral disc of FIG. 4.
Figure 5B:
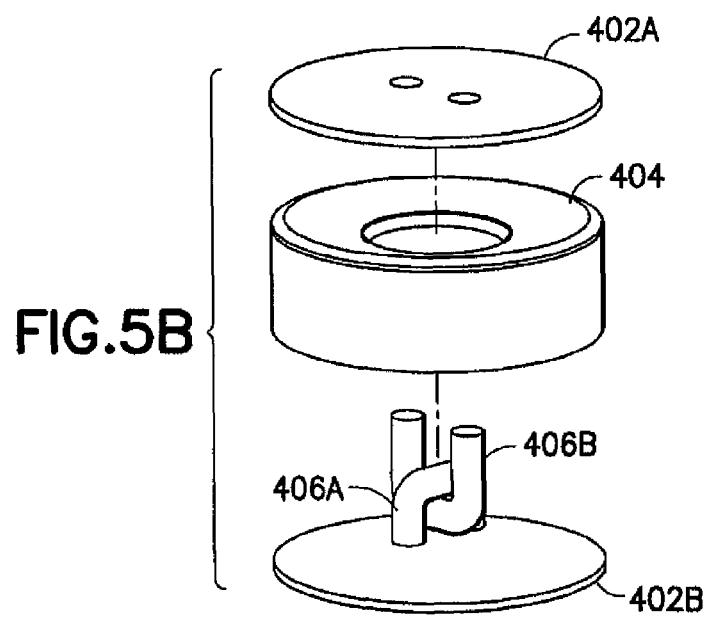
Figure 5C:
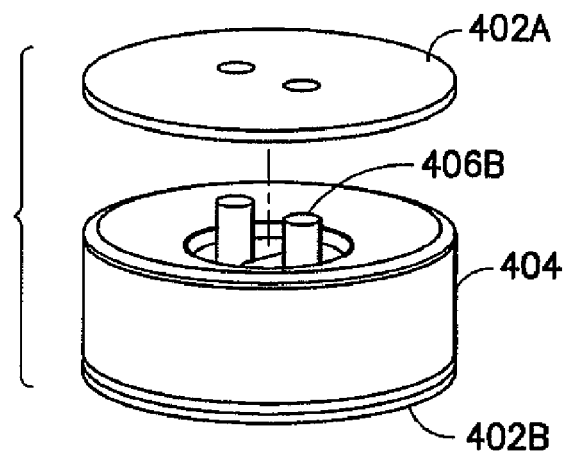
Figure 5D:
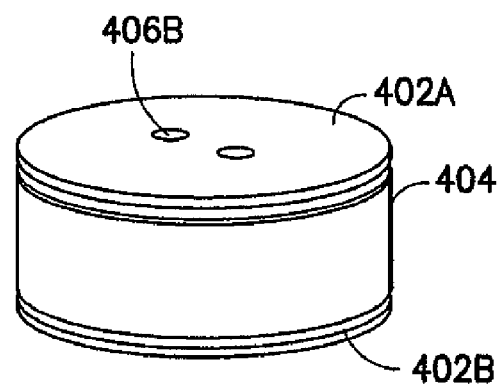

Referring now to FIG. 4, it is seen that Artificial Intervertebral Disc 400 includes First Anchor Plate 402A and Second Anchor Plate 402B (each Anchor Plate 402A, 402B may comprise, for example (which example is intended to be illustrative and not restrictive), any desired biologically acceptable metal). Of note, each Anchor Plate 402A, 402B may have an outer surface configured to be disposed adjacent a respective vertebral endplate (not shown). Further, Core 404 (e.g., comprising an elastomer) is sandwiched between an inner surface of Anchor Plate 402A and an inner surface of Anchor Plate 402B (in one example (which example is intended to be illustrative and not restrictive), the inner surfaces of Anchor Plates 402A, 402B may be convex and may be received in respective concavities in Core 404). In addition, First Chain Link 406A and Second Chain Link 406B (e.g., each of which may comprise a polymer and/or a metallic material (e.g., including a biologically acceptable metal)) are attached to Anchor Plates 402A, 402B. That is, First Chain Link 406A is attached at its open end to Anchor Plate 402B and second Chain Link 406B is attached at its open end to Anchor Plate 402A (when attached to the respective anchor plates the chain links interlock one another; in addition, the interlocking chain links run from Anchor Plate 402A to Anchor Plate 402B through a hole disposed in Core 404).

In one example (which example is intended to be illustrative and not restrictive), First Chain Link 406A may be attached to Anchor Plate 402B at depressions formed in an inner surface of Anchor Plate 402B and Second Chain Link 406B may be attached to Anchor Plate 402A at depressions formed in an inner surface of Anchor Plate 402A. In another example (which example is intended to be illustrative and not restrictive), First Chain Link 406A may be attached to Anchor Plate 402B via holes formed all the way through Anchor Plate 402B (i.e., holes extending from an inner surface of Anchor Plate 402B to an outer surface of Anchor Plate 402B) and Second Chain Link 406B may be attached to Anchor Plate 402A via holes formed all the way through Anchor Plate 402A (i.e., holes extending from an inner surface of Anchor Plate 402A to an outer surface of Anchor Plate 402A). In another example (which example is intended to be illustrative and not restrictive), First Chain Link 406A and Second Chain Link 406B may be attached to Anchor Plates 402A, 402B using any appropriate attachment mechanism (e.g., adhesive, welding, screw(s), bolt(s), friction fitting(s), etc.).

Referring now to FIGS. 5A-5D, example assembly steps (which examples are intended to be illustrative and not restrictive) associated with the artificial intervertebral disc of FIG. 4 are shown.

Figure 6:
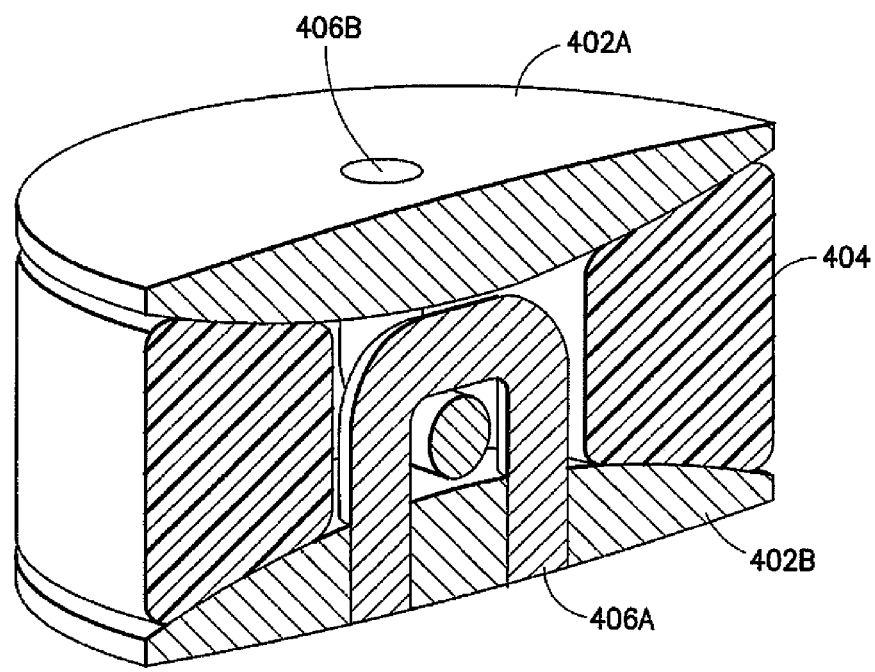
FIG. 6 shows a cut-away view of the assembled artificial intervertebral disc of FIG. 4.

Referring now to FIG. 6, a cut-away view of the assembled artificial intervertebral disc of FIG. 4 is shown.

Referring now to FIGS. 7A-7F, example initial fixation mechanisms (which examples are intended to be illustrative and not restrictive) associated with artificial intervertebral discs according to the present invention are shown.

Figure 7A:
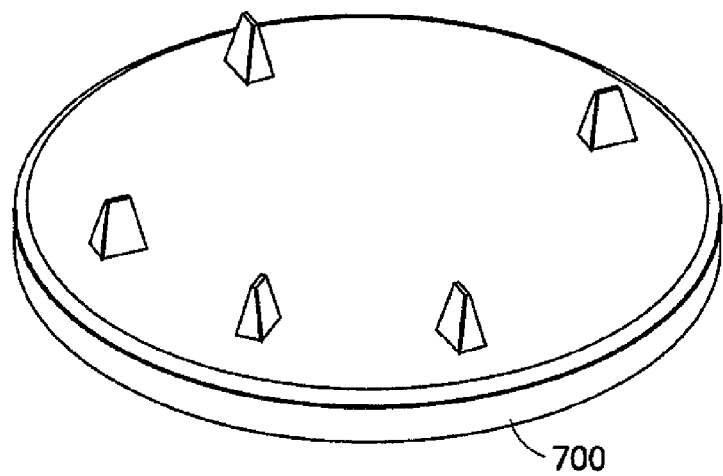
FIGS. 7A-7F show example initial fixation mechanisms associated with artificial intervertebral discs according to the present invention.
Figure 7B:
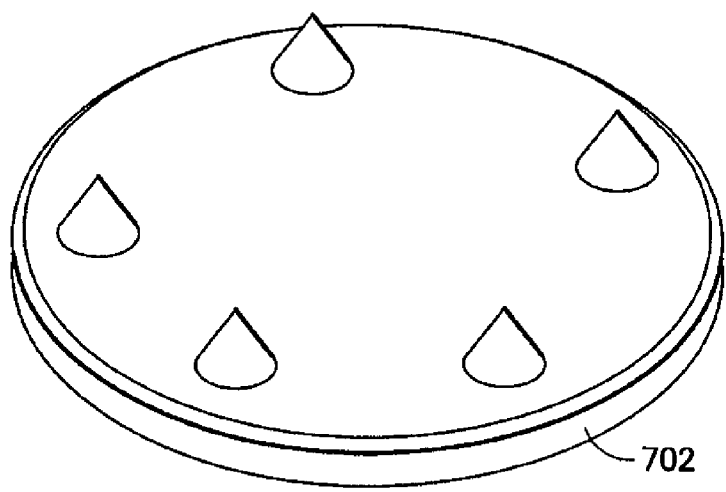
Figure 7C:
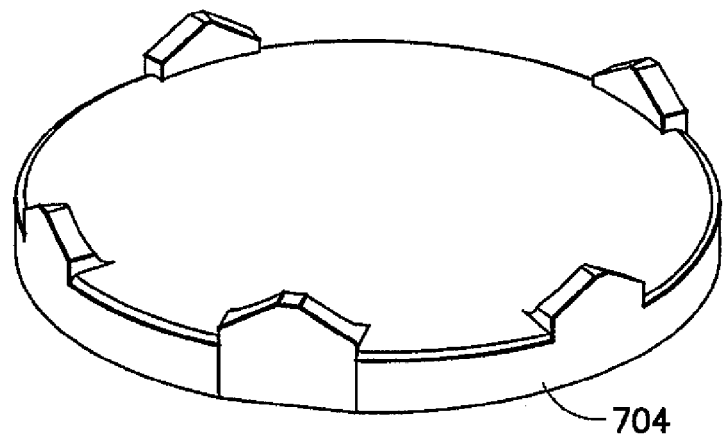
Figure 7D:
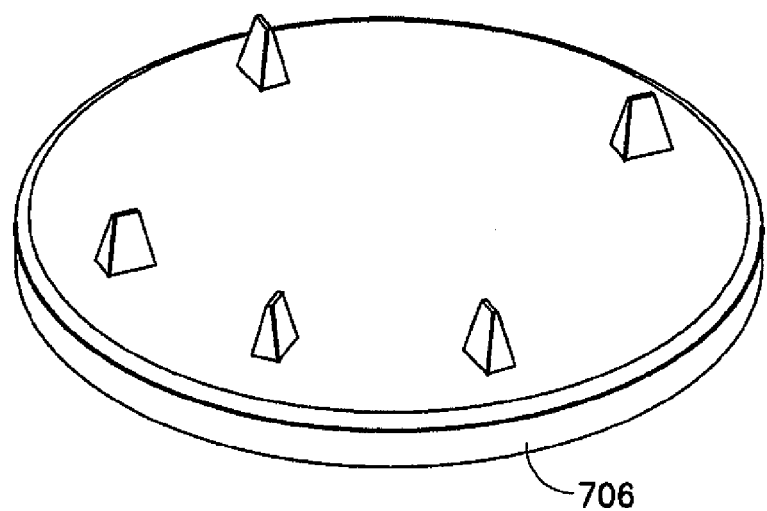
Figure 7E:
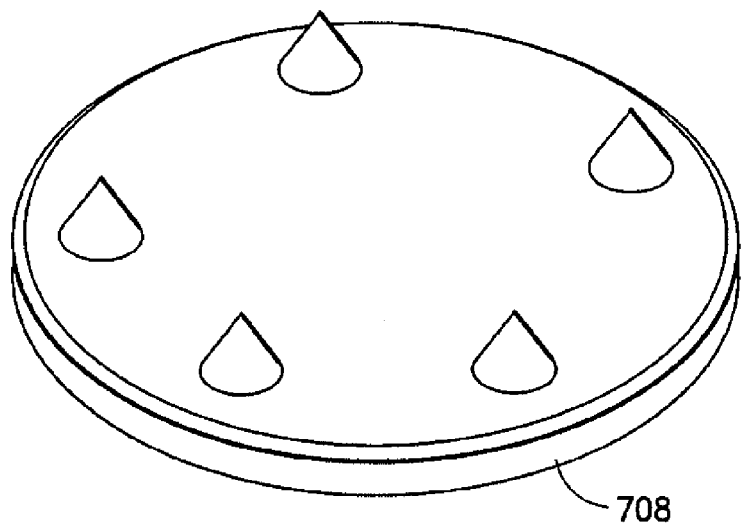
Figure 7F:
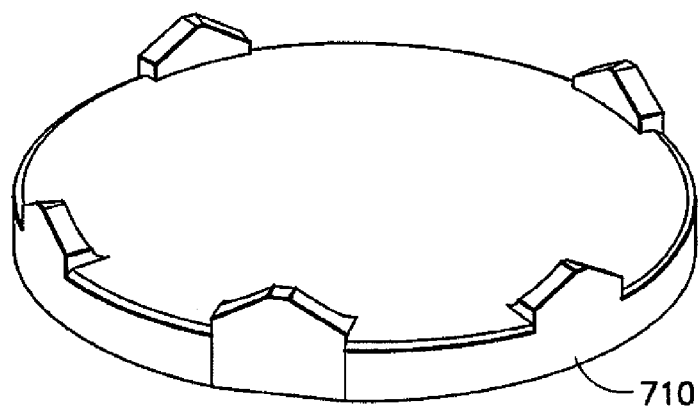

More particularly, FIG. 7A shows Anchor Member 700 having three pyramidal type protrusions for gripping a vertebral endplate (not shown); FIG. 7B shows Anchor Member 702 having three conical type protrusions for gripping a vertebral endplate (not shown); FIG. 7C shows Anchor Member 704 having three spade or keel type protrusions for gripping a vertebral endplate (not shown); FIG. 7D shows Anchor Member 706 having five pyramidal type protrusions for gripping a vertebral endplate (not shown); FIG. 7E shows Anchor Member 708 having five conical type protrusions for gripping a vertebral endplate (not shown); and FIG. 7F shows Anchor Member 710 having five spade or keel type protrusions for gripping a vertebral endplate (not shown). Of course, any desired number and/or placement of such initial fixation mechanisms may be utilized.

Referring now to FIG. 8 (showing another embodiment of the present invention), it is seen that Artificial Intervertebral Disc 800 includes First Anchor Plate 802A and Second Anchor Plate 802B (each Anchor Plate 802A, 802B may comprise, for example (which example is intended to be illustrative and not restrictive), any desired biologically acceptable metal). Of note, each Anchor Plate 802A, 802B may have an outer surface configured to be disposed adjacent a respective vertebral endplate (not shown). Further, Column Filler 804 (e.g., comprising an elastomer) is sandwiched between an inner surface of Anchor Plate 802A and an inner surface of Anchor Plate 802B (in one example (which example is intended to be illustrative and not restrictive), the inner surfaces of Anchor Plates 802A, 802B may be concave for receiving therein Column Filler 804). In addition, Column 806 (e.g., comprising DACRON) is held between First Inner Ring 808A and First Outer Ring 808B as well as between Second Inner Ring 810A and Second Outer Ring 810B for attachment to each of Anchor Plates 802A, 802B.

In one example (which example is intended to be illustrative and not restrictive), Column 806 is held between First Inner Ring 808A and First Outer Ring 808B as well as between Second Inner Ring 810A and Second Outer Ring 810B by crimping or rotary swaging.

In another example (which example is intended to be illustrative and not restrictive), Column 806 is held between respective inner and outer rings for attachment to each of Anchor Plates 802A, 802B (such as, for example, on outside vertical surfaces of Anchor Plates 802A, 802B) by welding (e.g., laser welding) First Inner Ring 808A to Anchor Plate 802A and Second Inner Ring 810A to Anchor Plate 802B.

Referring now to FIGS. 9-12 (showing another embodiment of the present invention), it is seen that Artificial Intervertebral Disc 900 includes First Anchor Plate 902A and Second Anchor Plate 902B (each Anchor Plate 902A, 902B may comprise, for example (which example is intended to be illustrative and not restrictive), any desired biologically acceptable metal). Of note, each Anchor Plate 902A, 902B may have an outer surface configured to be disposed adjacent a respective vertebral endplate (not shown). Further, Column Filler 904 (e.g., comprising an elastomer) is disposed between an inner surface of Anchor Plate 902A and an inner surface of Anchor Plate 902B (in one example (which example is intended to be illustrative and not restrictive), the inner surfaces of Anchor Plates 902A, 902B may be concave for receiving therein Column Filler 904). In addition, Column 906 (e.g., comprising DACRON) is held between First Inner Ring 908A and First Outer Ring 908B as well as between Second Inner Ring 910A and Second Outer Ring 910B for attachment to each of Anchor Plates 902A, 902B.

Still referring to FIGS. 9-12, it is noted that each of First Anchor Plate 902A and Second Anchor Plate 902B may include Spikes 912 (e.g., to aid in initial fixation), Pockets 914 (e.g., for holding a porous coating), and/or Attachment Features (e.g., for interface with one or more holding/implantation instruments).

Figure 9:
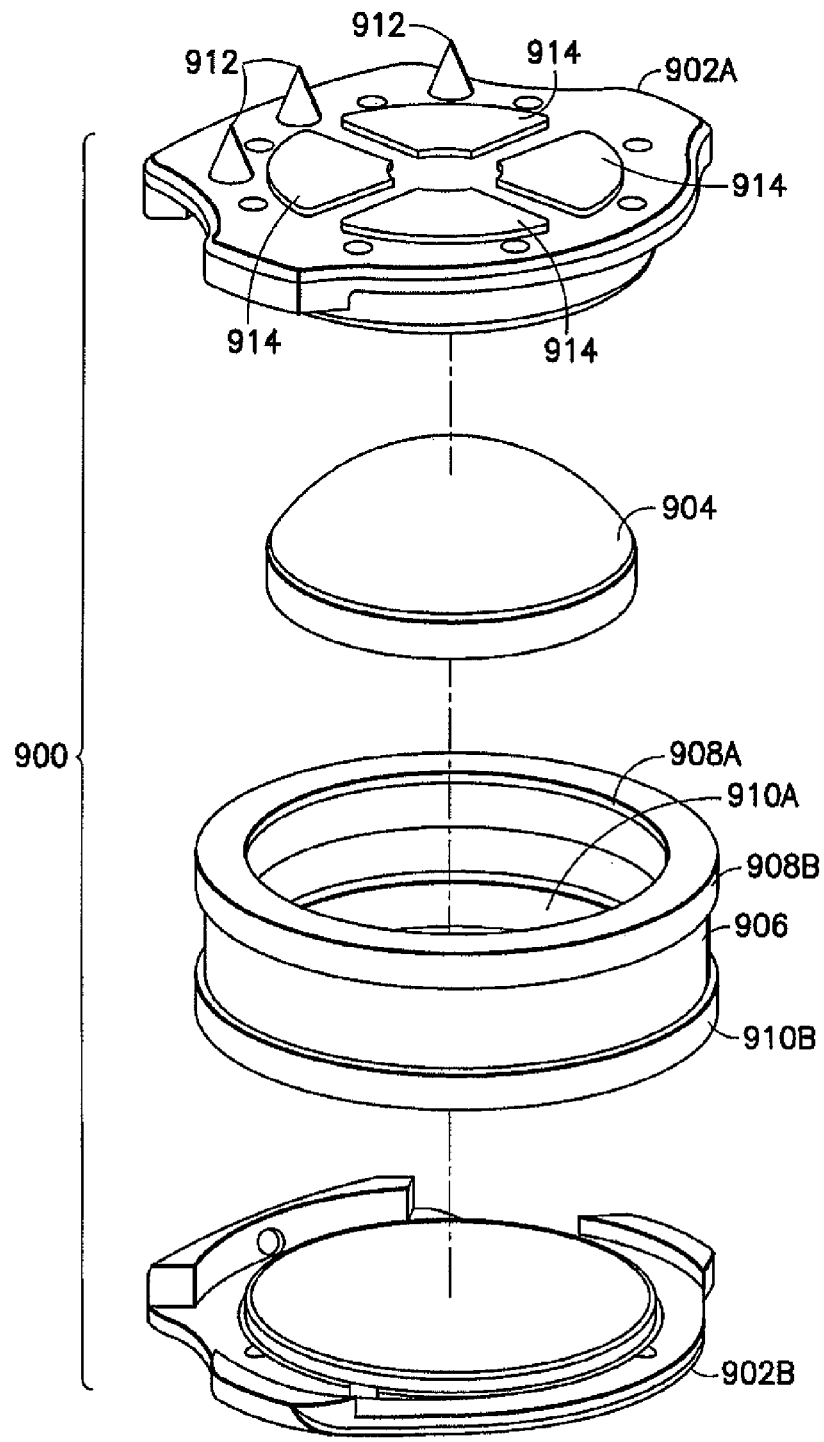
FIG. 9 shows an exploded view of an artificial intervertebral disc according to another embodiment of the present invention.
Figure 10:
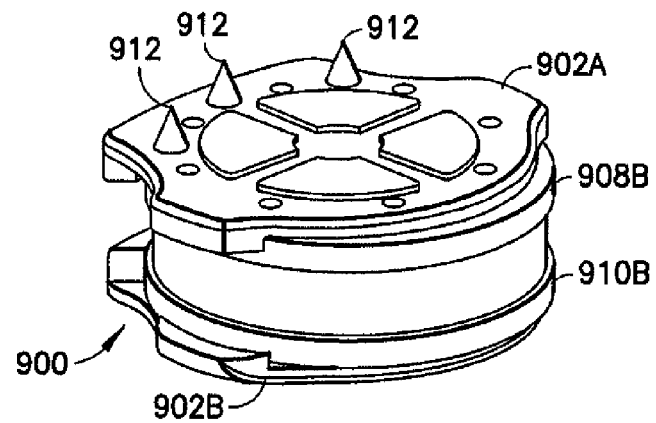
FIG. 10 shows a perspective view of the artificial intervertebral disc of FIG. 9.
Figure 11:
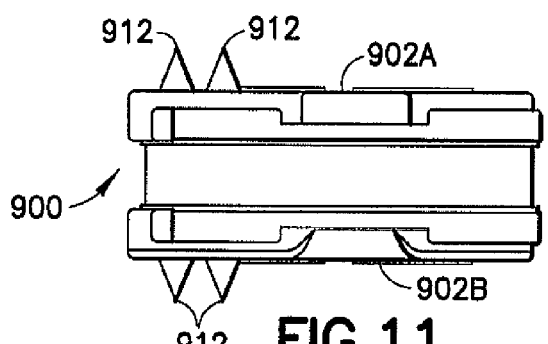
FIG. 11 shows a side view of the artificial intervertebral disc of FIG. 9.
Figure 12:
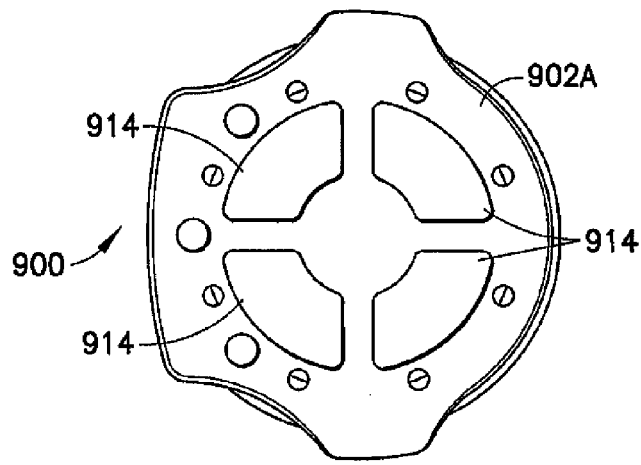
FIG. 12 shows a top view of the artificial intervertebral disc of FIG. 9.
Figure 13A:
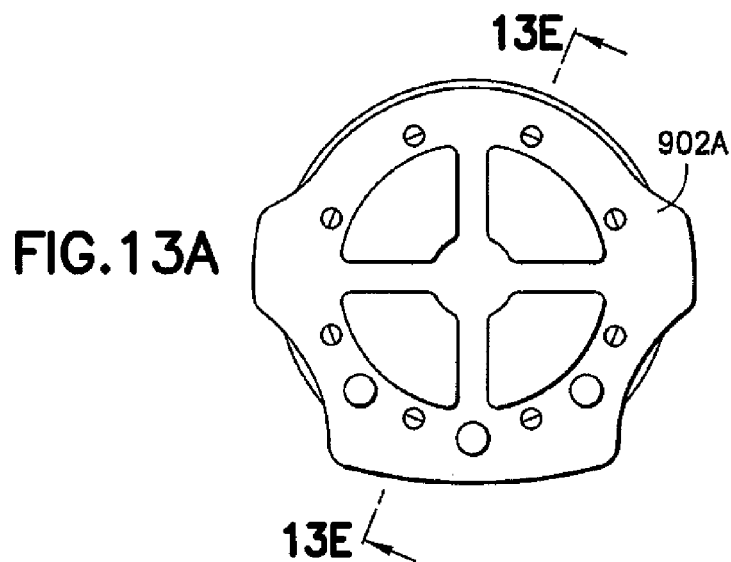
FIGS. 13A-13F show additional details of the artificial intervertebral disc of FIG. 9 (FIG. 13A is a top view, FIG. 13B is a bottom view, FIG. 13C is a side view, FIG. 13D is a side view, FIG. 13E is a side cut-away view (along section B-B of FIG. 13A) and FIG. 13F is a detail view of portion "C" of FIG. 13E)
Figure 13B:
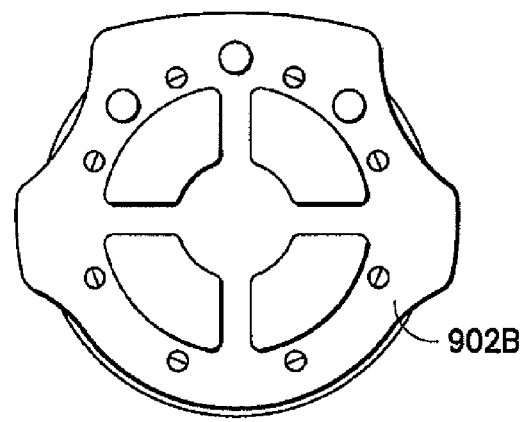
Figure 13C:
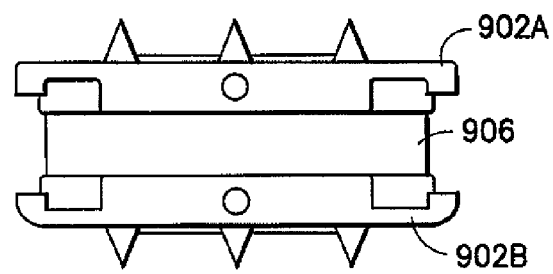
Figure 13D:
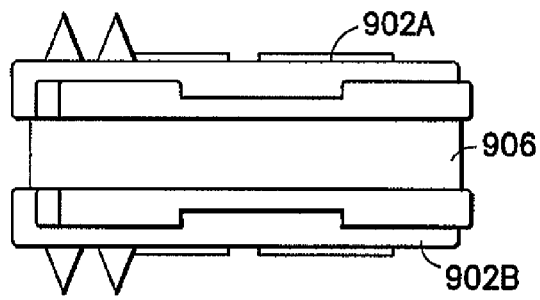
Figure 13E:
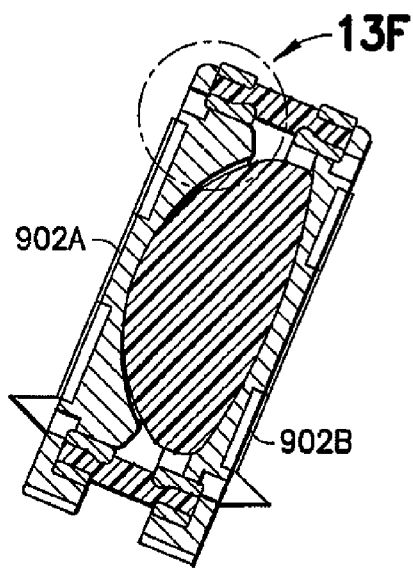
Figure 13F:
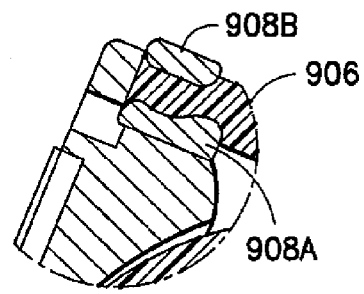

Referring now to FIGS. 13A-13F, additional details of the artificial intervertebral disc of FIG. 9 are shown. In this regard, FIG. 13A is a top view, FIG. 13B is a bottom view, FIG. 13C is a side view, FIG. 13D is a side view, FIG. 13E is a side cut-away view (along section B-B of FIG. 13A) and FIG. 13F is a detail view of portion "C" of FIG. 13E.

Figure 14A:
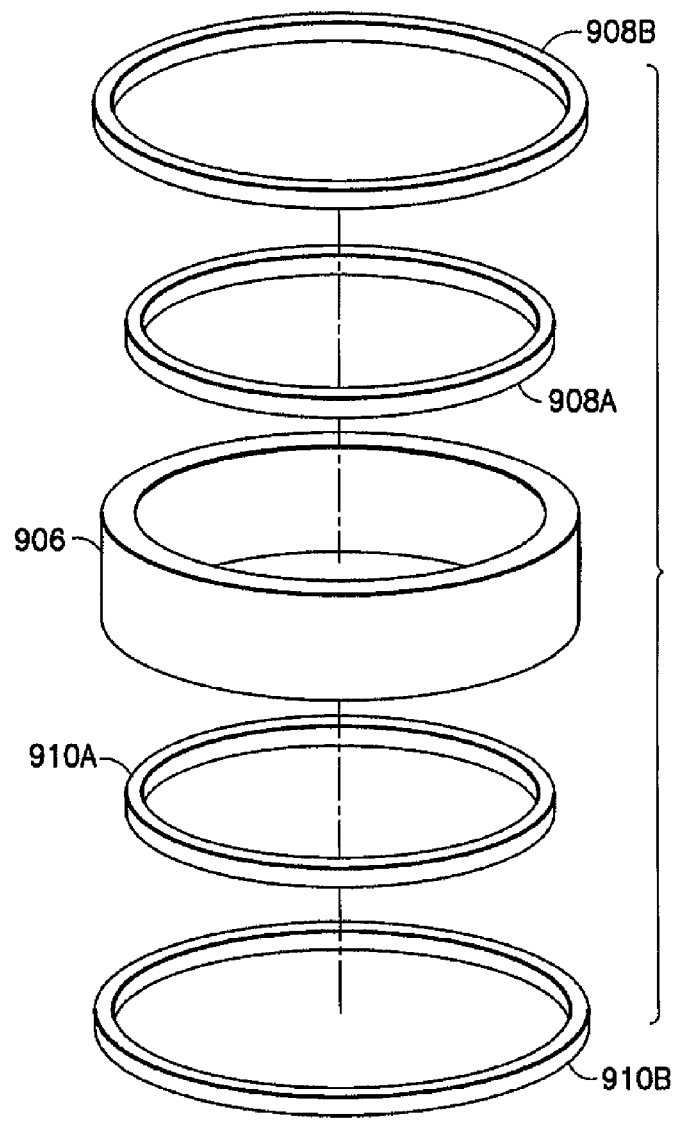
FIGS. 14A-14D show additional details of a column and crimp rings of the artificial intervertebral disc of FIG. 9 (FIG. 14A is an exploded view, FIG. 14B is a top view, FIG. 14C is a side cut-away view (along section A-A of FIG. 14B) and FIG. 14D is a detail view of a portion of FIG. 14C)
Figure 14B:
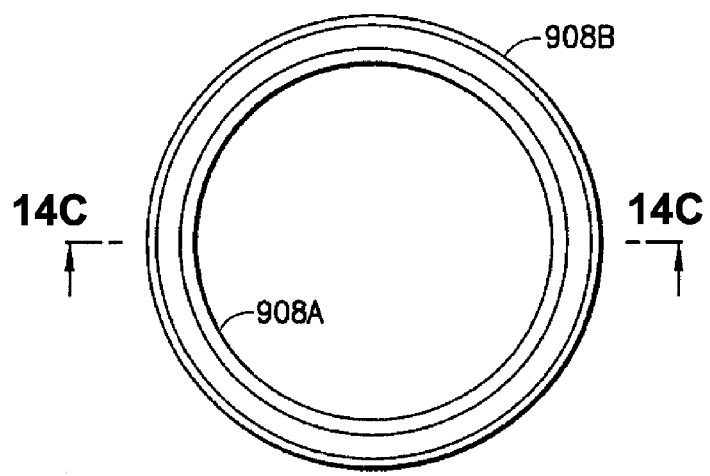
Figure 14C:
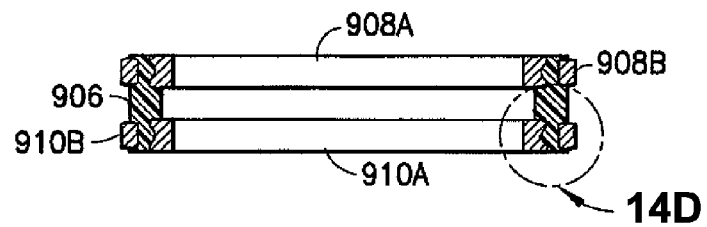
Figure 14D:
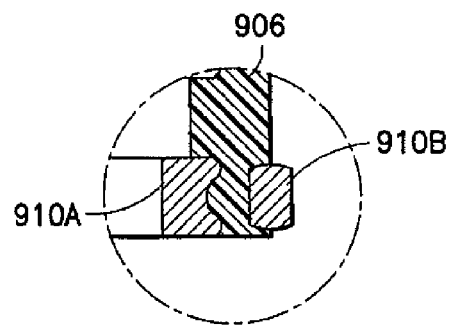

Referring now to FIGS. 14A-14D, additional details of a column and crimp rings of the artificial intervertebral disc of FIG. 9 are shown In this regard, FIG. 14A is an exploded view, FIG. 14B is a top view, FIG. 14C is a side cut-away view (along section A-A of FIG. 14B) and FIG. 14D is a detail view of a portion of FIG. 14C.

Figure 15A:
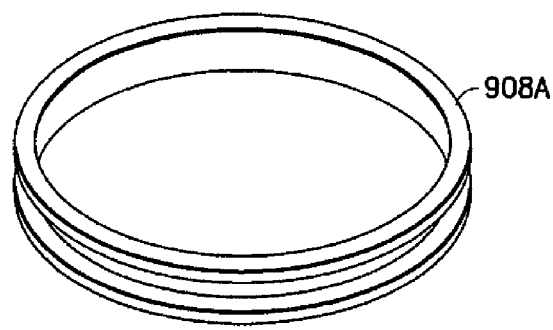
FIGS. 15A-15C show additional details of an inner crimp ring of the artificial intervertebral disc of FIG. 9 (FIG. 15A is a perspective view, FIG. 15B is a top view and FIG. 15C is a side cut-away view (along section A-A of FIG. 15B))
Figure 15B:
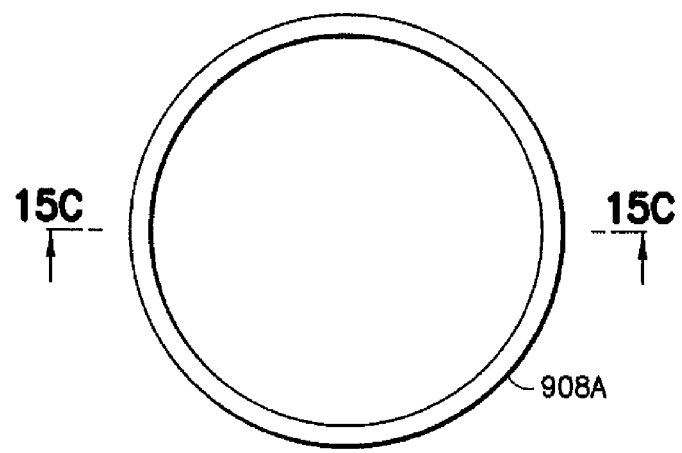
Figure 15C:

Referring now to FIGS. 15A-15C, additional details of an inner crimp ring of the artificial intervertebral disc of FIG. 9 are shown. In this regard, FIG. 15A is a perspective view, FIG. 15B is a top view and FIG. 15C is a side cut-away view (along section A-A of FIG. 15B).

Figure 16A:
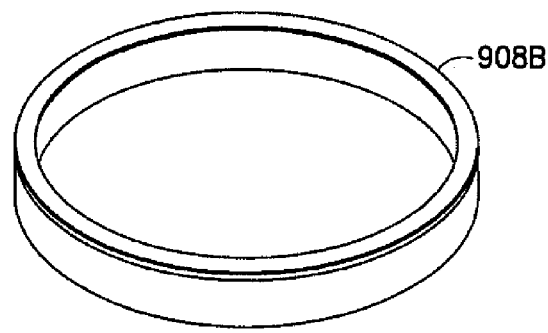
FIGS. 16A-16C show additional details of an outer crimp ring of the artificial intervertebral disc of FIG. 9 (FIG. 16A is a perspective view, FIG. 16B is a top view and FIG. 16C is a side cut-away view (along section A-A of FIG. 16B))
Figure 16B:
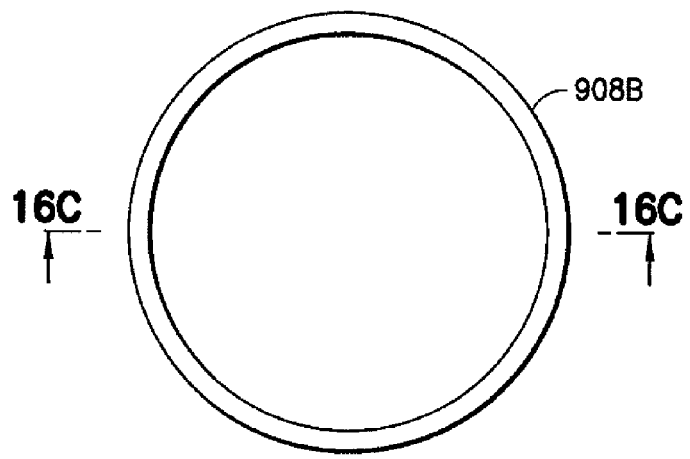
Figure 16C:
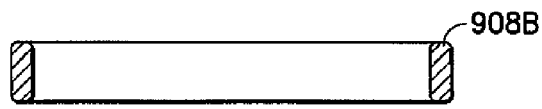

Referring now to FIGS. 16A-16C, additional details of an outer crimp ring of the artificial intervertebral disc of FIG. 9 are shown. In this regard, FIG. 16A is a perspective view, FIG. 16B is a top view and FIG. 16C is a side cut-away view (along section A-A of FIG. 16B).

Figure 17A:
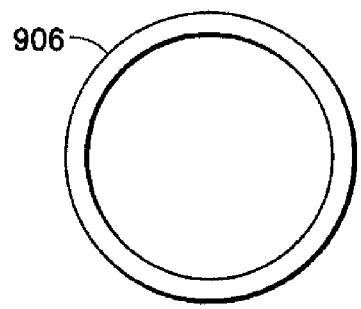
FIGS. 17A and 17B show additional details of a column of the artificial intervertebral disc of FIG. 9 (FIG. 17A is a top view and FIG. 17B is a side view)
Figure 17B:
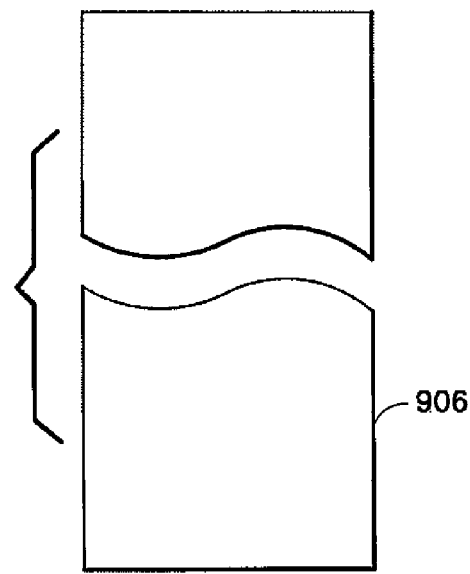

Referring now to FIGS. 17A and 17B, additional details of a column of the artificial intervertebral disc of FIG. 9 are shown. In this regard, FIG. 17A is a top view and FIG. 17B is a side view.

Figure 18A:
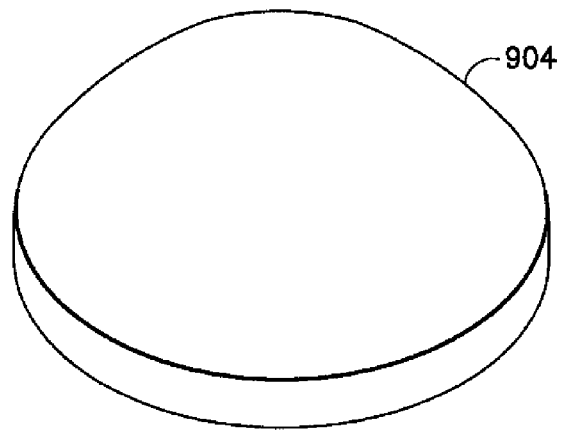
FIGS. 18A and 18B show additional details of a column filler of the artificial intervertebral disc of FIG. 9 (FIG. 18A is a perspective view and FIG. 18B is a side view)
Figure 18B:
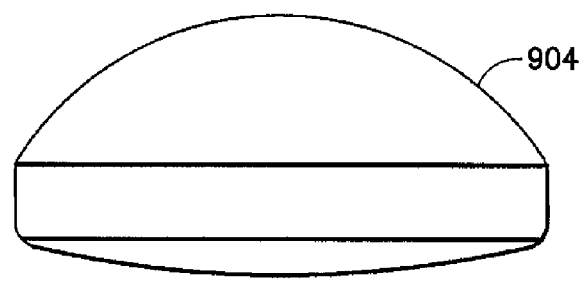
Figure 19A:
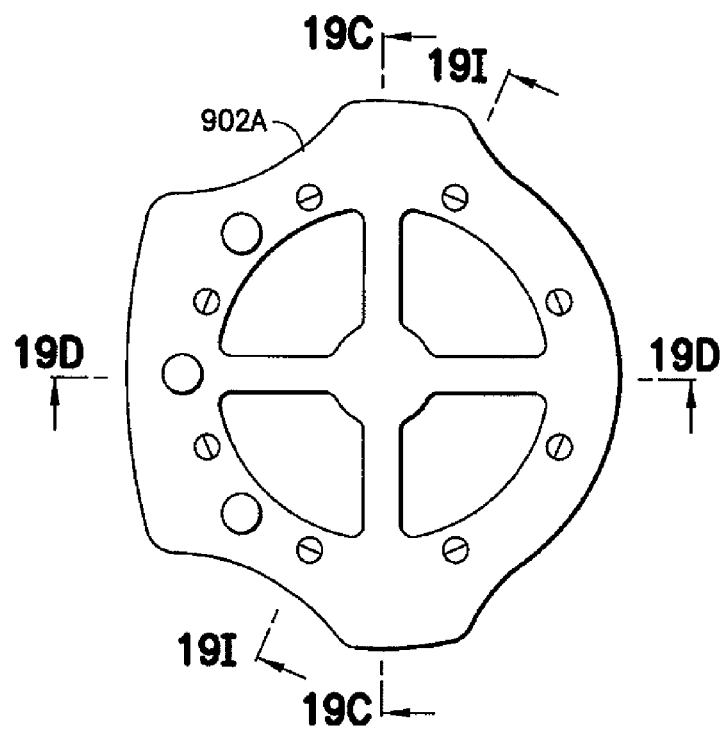
FIGS. 19A-19I show additional details of an upper (i.e., caphalad) anchor plate of the artificial intervertebral disc of FIG. 9.
Figure 19B:
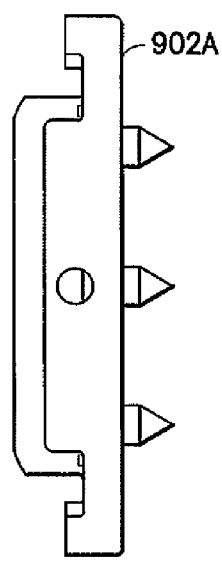
Figure 19C:
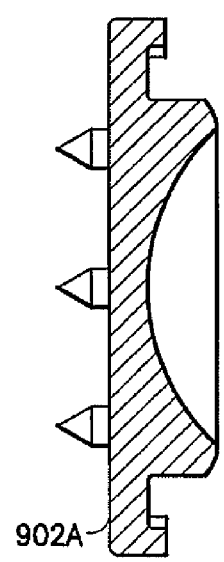
Figure 19D:
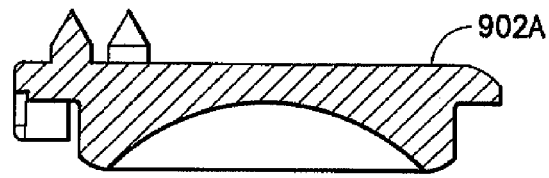
Figure 19E:
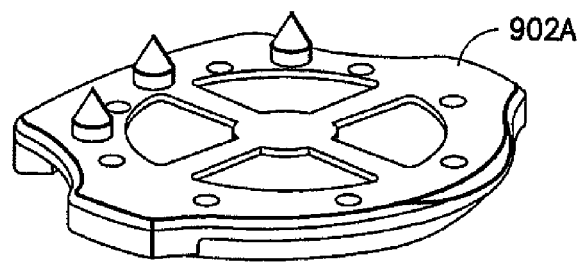
Figure 19F:
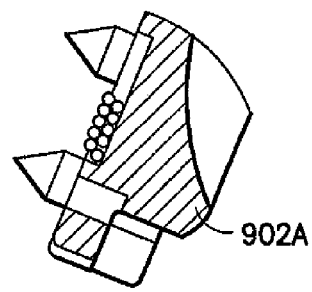
Figure 19G:
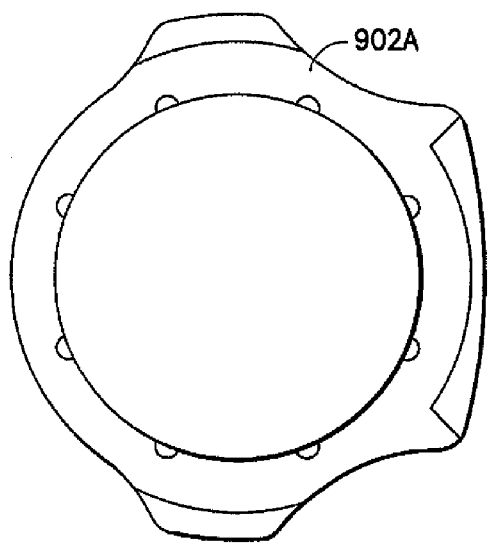
Figure 19H:
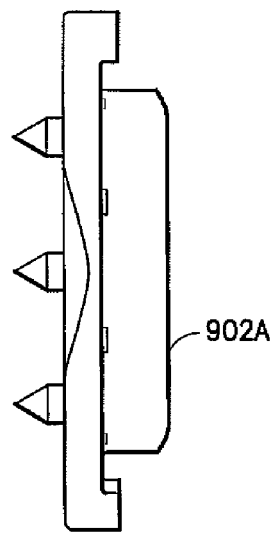
Figure 19I:
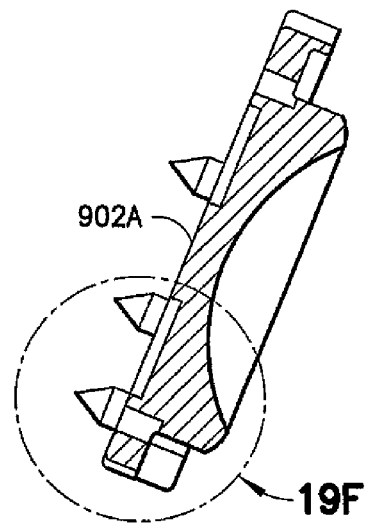
Figure 20A:
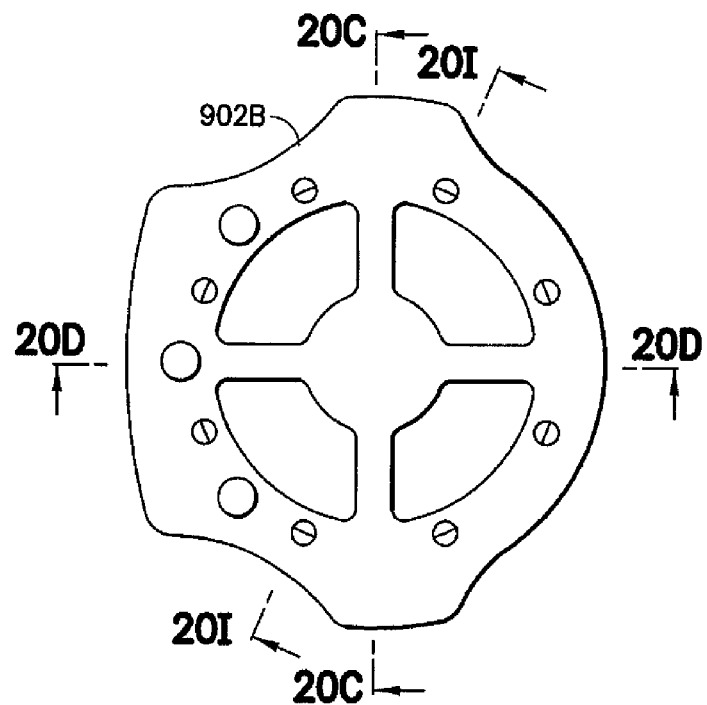
FIGS. 20A-20I show additional details of a lower (i.e., caudal) anchor plate of the artificial intervertebral disc of FIG. 9.
Figure 20B:
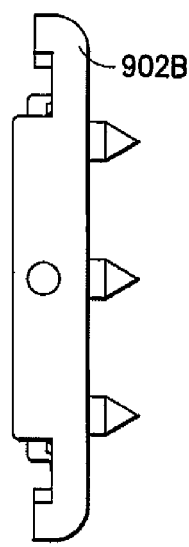
Figure 20C:
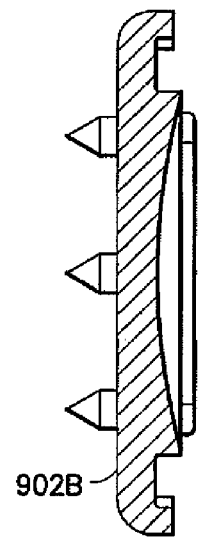
Figure 20D:
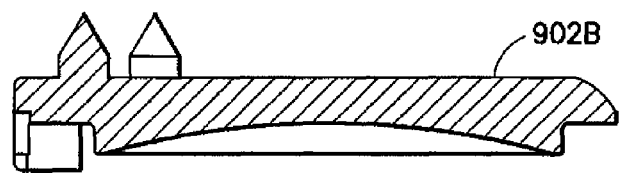
Figure 20E:
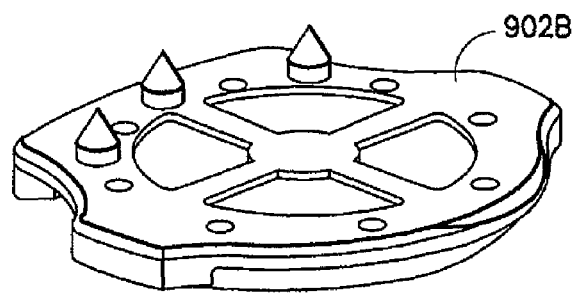
Figure 20F:
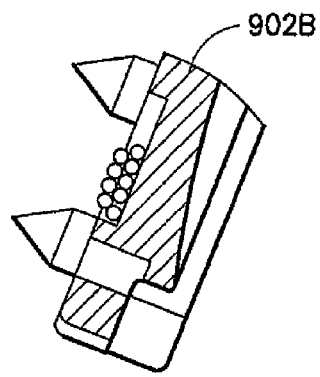
Figure 20G:
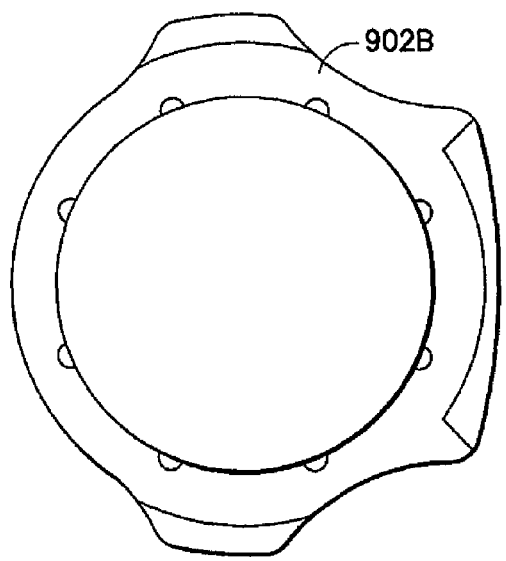
Figures 20H, 20I:
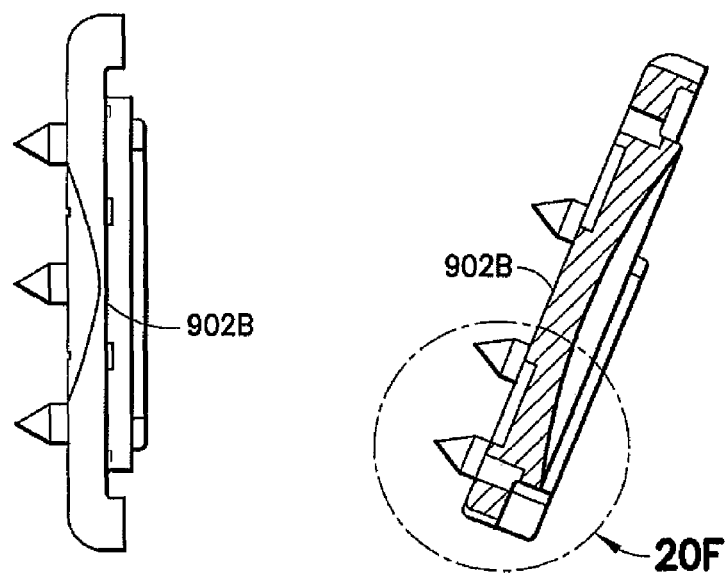

Referring now to FIGS. 18A and 18B, additional details of a column filler of the artificial intervertebral disc of FIG. 9 are shown. In this regard, FIG. 17A is a perspective view and FIG. 17B is a side view.

Referring now to FIGS. 19A-19I, additional details of an upper (i.e., cephalad) anchor plate of the artificial intervertebral disc of FIG. 9 are shown.

Referring now to FIGS. 20A-20I, additional details of a lower (i.e., caudal) anchor plate of the artificial intervertebral disc of FIG. 9 are shown.

Figure 21:
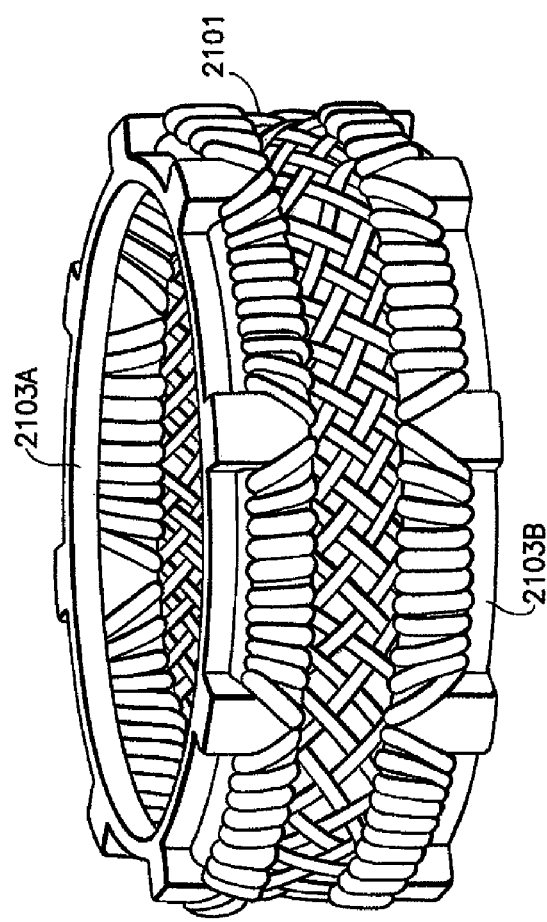
FIG. 21 shows a perspective view of an artificial intervertebral disc according to another embodiment of the present invention.

Referring now to FIG. 21, portions of an artificial intervertebral disc according to another embodiment of the present invention are shown. As seen in this FIG. 21, Column 2101 (e.g., comprising DACRON) is threaded between Upper Ring 2103A and Lower Ring 2103B. Although not shown in this FIG. 21 for clarity, each of Upper Ring 2103A and Lower Ring 2103B is attached (e.g., by welding) to a respective Upper Anchor Plate and Lower Anchor Plate (each Upper Anchor Plate and Lower Anchor Plate may comprise, for example (which example is intended to be illustrative and not restrictive), any desired biologically acceptable metal). Further, each Upper Anchor Plate and Lower Anchor Plate may have an outer surface configured to be disposed adjacent a respective vertebral endplate (not shown). Moreover, although not shown in this FIG. 21 for clarity, Column Filler (e.g., comprising an elastomer) is disposed inside of Column 2101 (in one example (which example is intended to be illustrative and not restrictive), the inner surfaces of the Upper and Lower Anchor Plates may be concave for receiving therein the Column Filler).

Figure 22A:
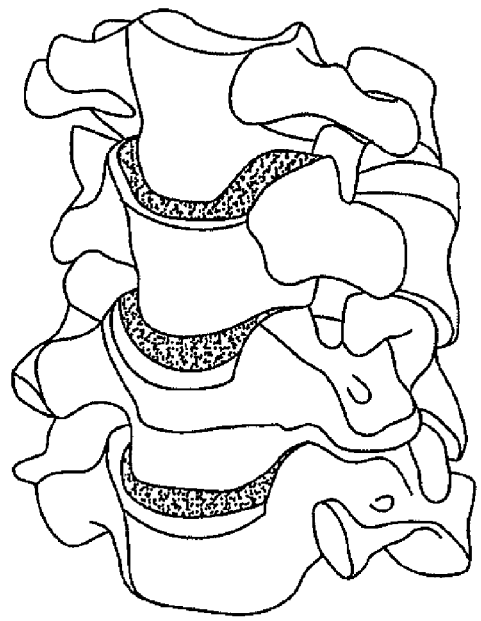
FIGS. 22A-22N show diagrams of a surgical technique associated with the present invention.
Figure 22B:
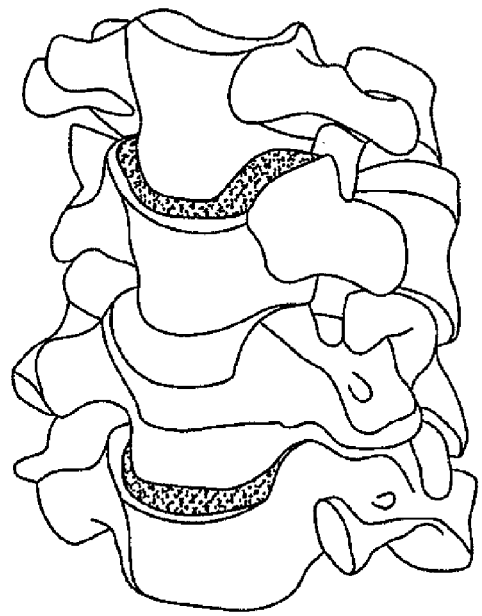
Figures 22C, 22D:
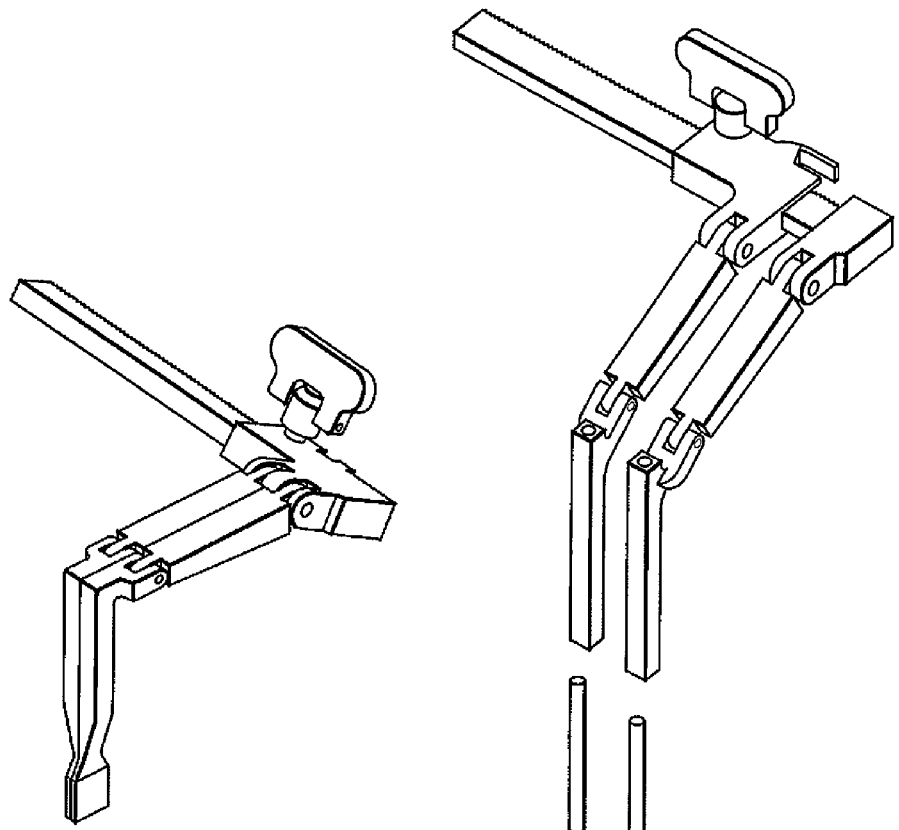
Figures 22E, 22F, 22G:
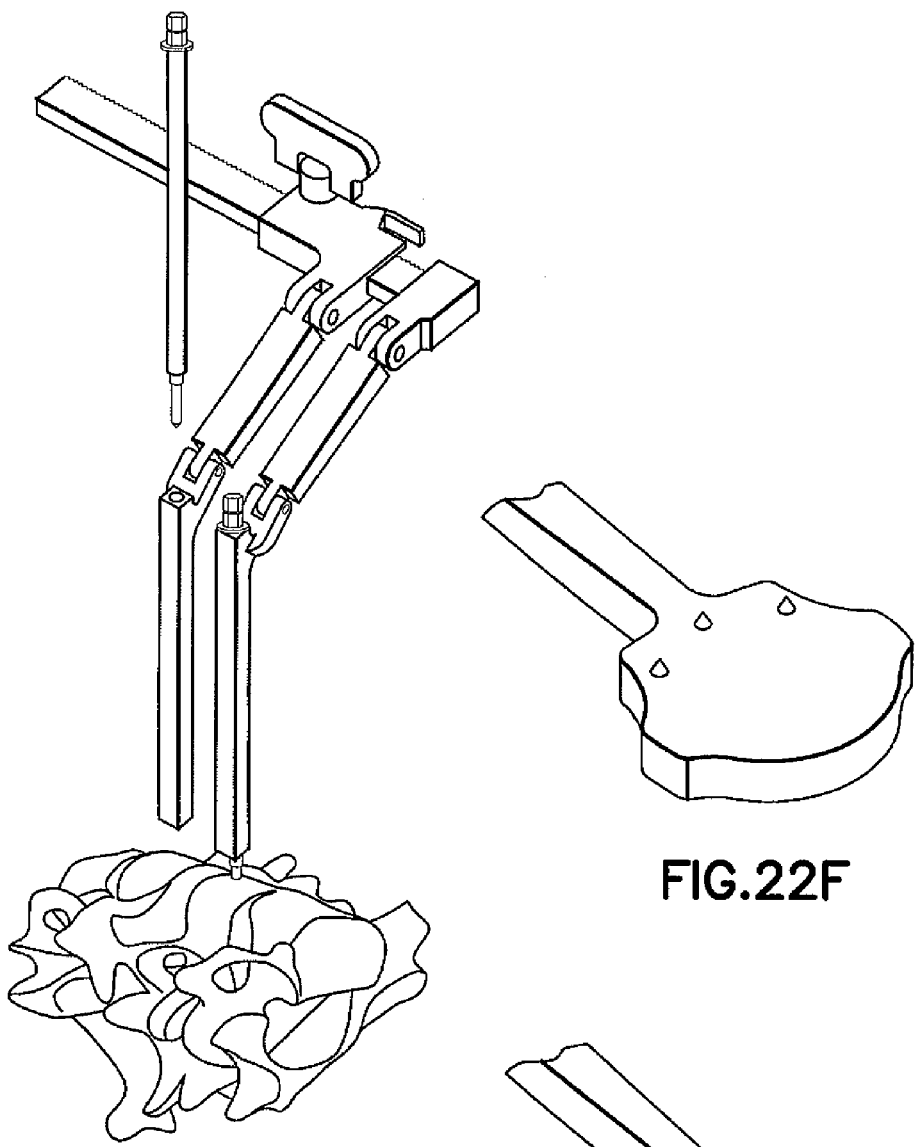
Figure 22H:
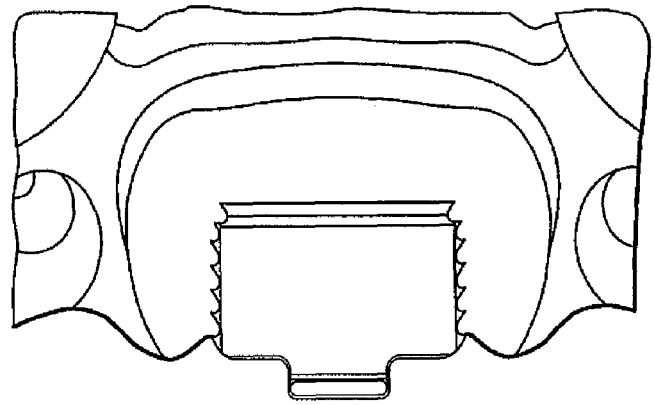
Figure 22I:
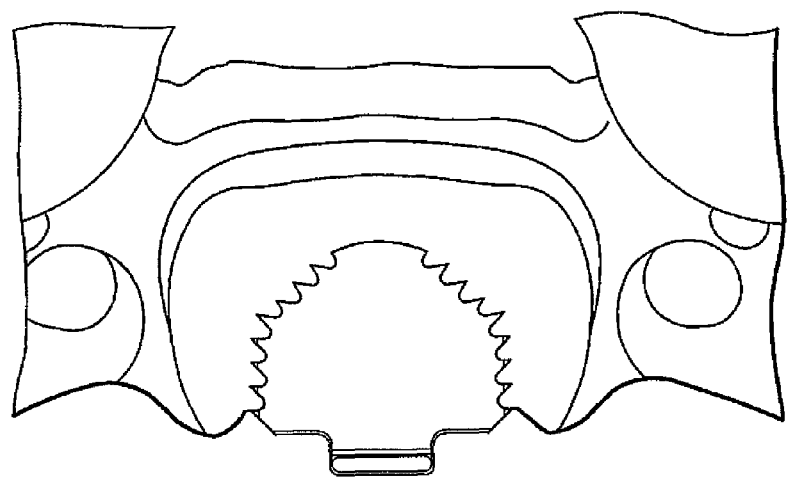
Figures 22J, 22K, 22L:
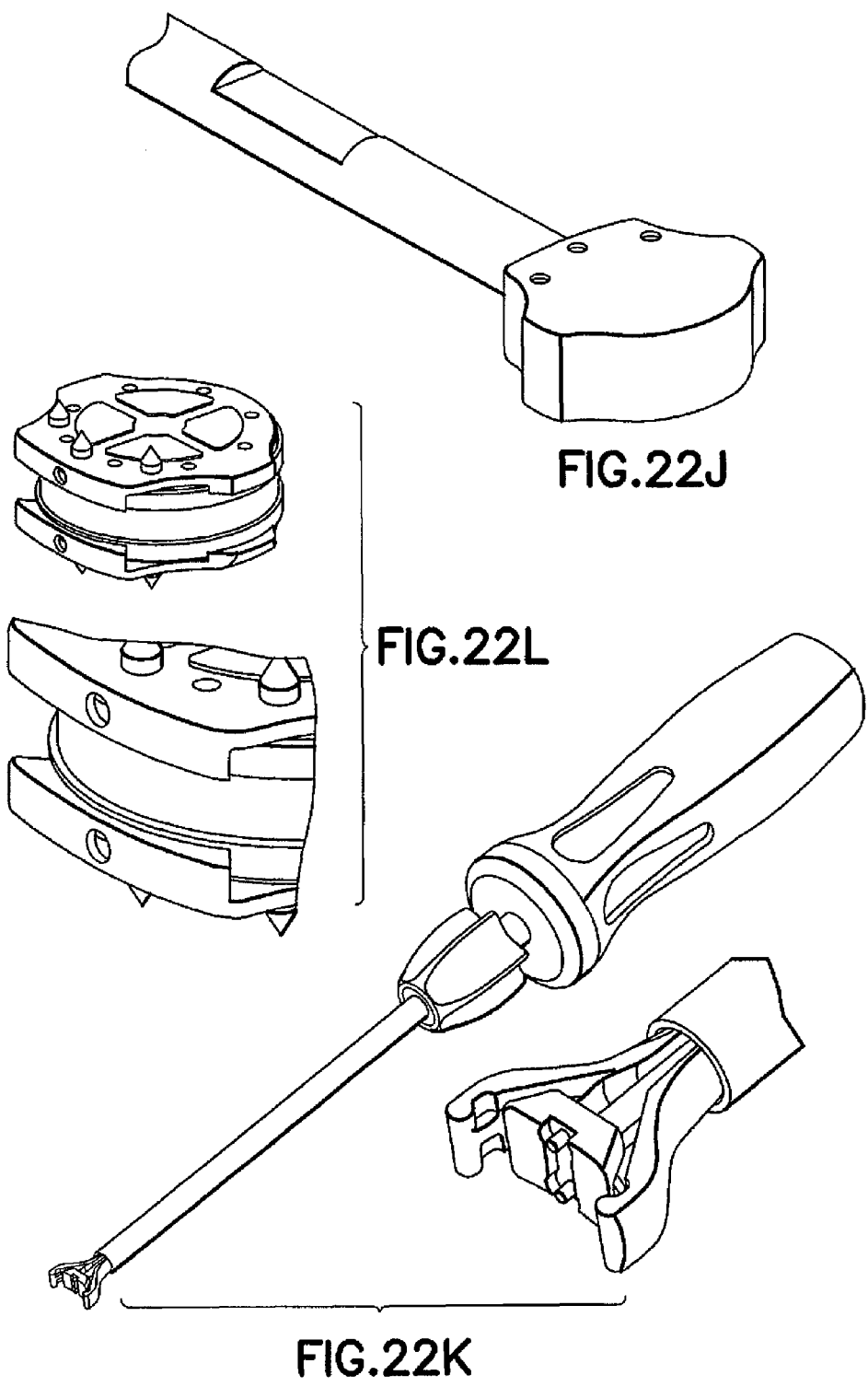
Figure 22M:
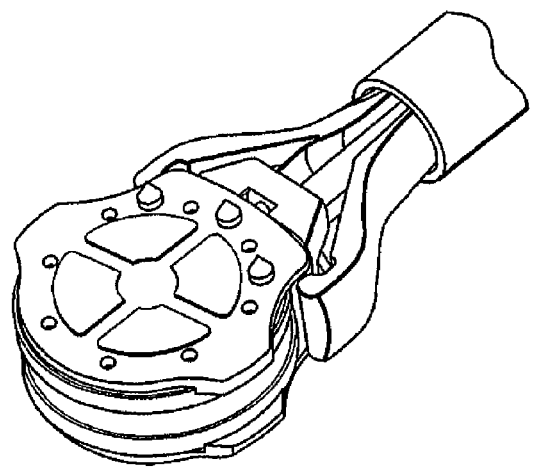
Figure 22N:
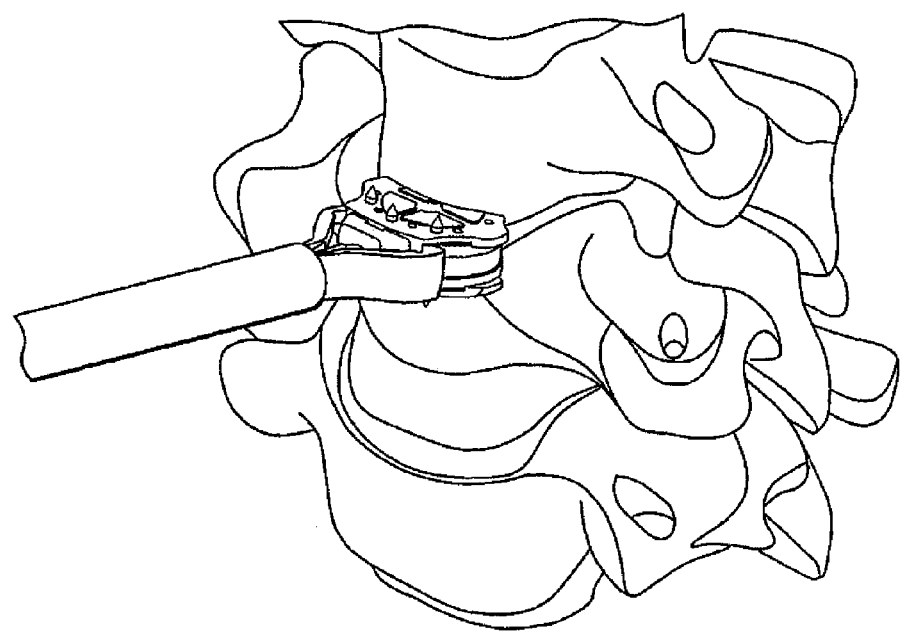

Referring now to FIGS. 22A-22N, diagrams of a surgical technique associated with the present invention are shown.

More particularly, it is noted that one example of a surgical technique associated with the present invention (which example is intended to be illustrative and not restrictive), may comprise the following steps.

Step 1, Access: Standard surgical approach to obtain adequate visualization of the affected disc space (see FIG. 22A).

Step 2, Discectomy: Evacuate the affected disc space using standard surgical procedures (see FIG. 22B).

Step 3.1, Distraction: Interbody distraction is achieved thru the use of the Blade-Style Distractor. Insert the blade end of the distractor into the interbody space, placing them as far posterior as possible (this technique will help achieve parallel spacing). Turn the ratcheting device until proper distraction has been achieved (see FIG. 22C).

Step 3.2, Distraction: Once parallel distraction of the interbody space has been achieved, (Blade Style Distractor may remain in place) the Pin Style Distractor is used to allow for access to the interbody space. Select desired pin styles. For Pin Style 1, insert pins into the anterior aspect of adjacent vertebral bodies. Once the pins are properly positioned, the canulated arms of the distractor can be positioned into place. The ratcheting device can then be actuated until proper distraction has been achieved. Remove the Blade Style Distractor. For Pin Style 2, place arms of the canulated distractor in place on adjacent vertebral bodies. Drive the hex top pins thru the canulated arms into the vertebral bodies. The ratcheting device can then be actuated until proper distraction has been achieved. Remove the Blade Style Distractor (see FIGS. 22D and 22E).

Step 4.1, Endplate Prep: End plate templates are provided to check that the vertebral endplate will match the implant. Check to make sure the template labeled "Top" is used for the inferior end plate of the Cephalad vertebral body and the template labeled "Bottom" is used for the superior end plate of the Caudal vertebral body (see FIGS. 22F and 22G).

Step 4.2, Endplate Prep: Shaping of the vertebral endplates, if required, can be achieved thru broaching. The first Broach (see FIG. 22H) is inserted into the disc space creating the M/L clearance for proper implant fit. Followed by the second broach (FIG. 22I), which removes the material from the posterior aspect of the joint space.

Step 5, Implant Height Evaluation. Trial Sizing: Selection of the proper implant is essential. Place the trials starting with the smallest (e.g., 6 mm) in the disc space to determine the proper implant size (height and footprint) (see FIG. 22J).

Step 6, Implant Insertion: Load the prosthetic device onto the holder by aligning pins on holder (see FIG. 22K) with holes on the implant (see FIG. 22L). Turn knob on holder to actuate the jaws until a snug fit has been achieved. Place the device into vertebral space using flouroscopy. Once satisfied with implant placement, turn knob on holder to release the jaws and pull instrument away from implant (see FIGS. 22M and 22N).

Figure 23A:
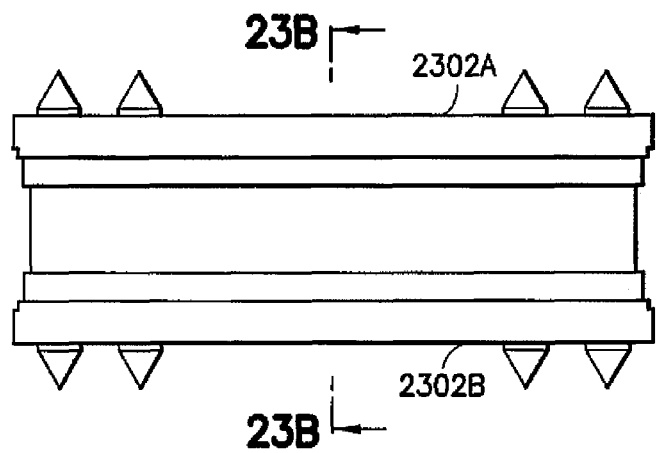
FIG. 23A shows a side view of an artificial intervertebral disc according to another embodiment of the present invention.
Figure 23B:
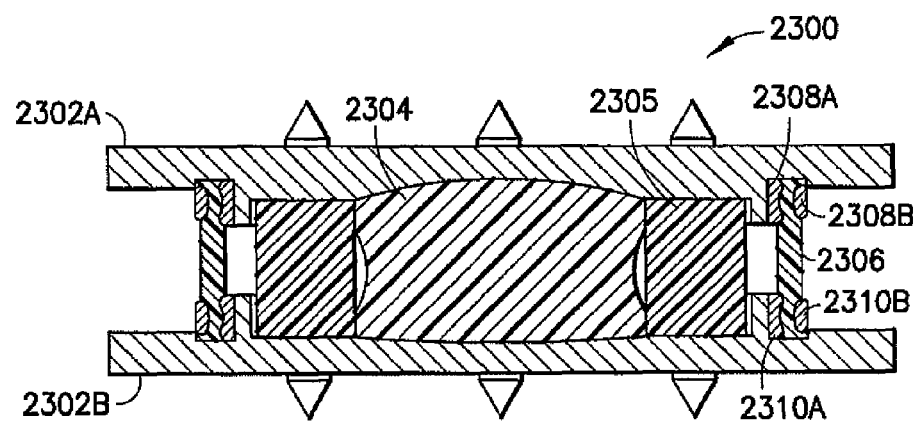
FIG. 23B shows a cross-sectional view of the artificial intervertebral disc of FIG. 23A (taken along line B-B of FIG. 23A)
Figure 24:
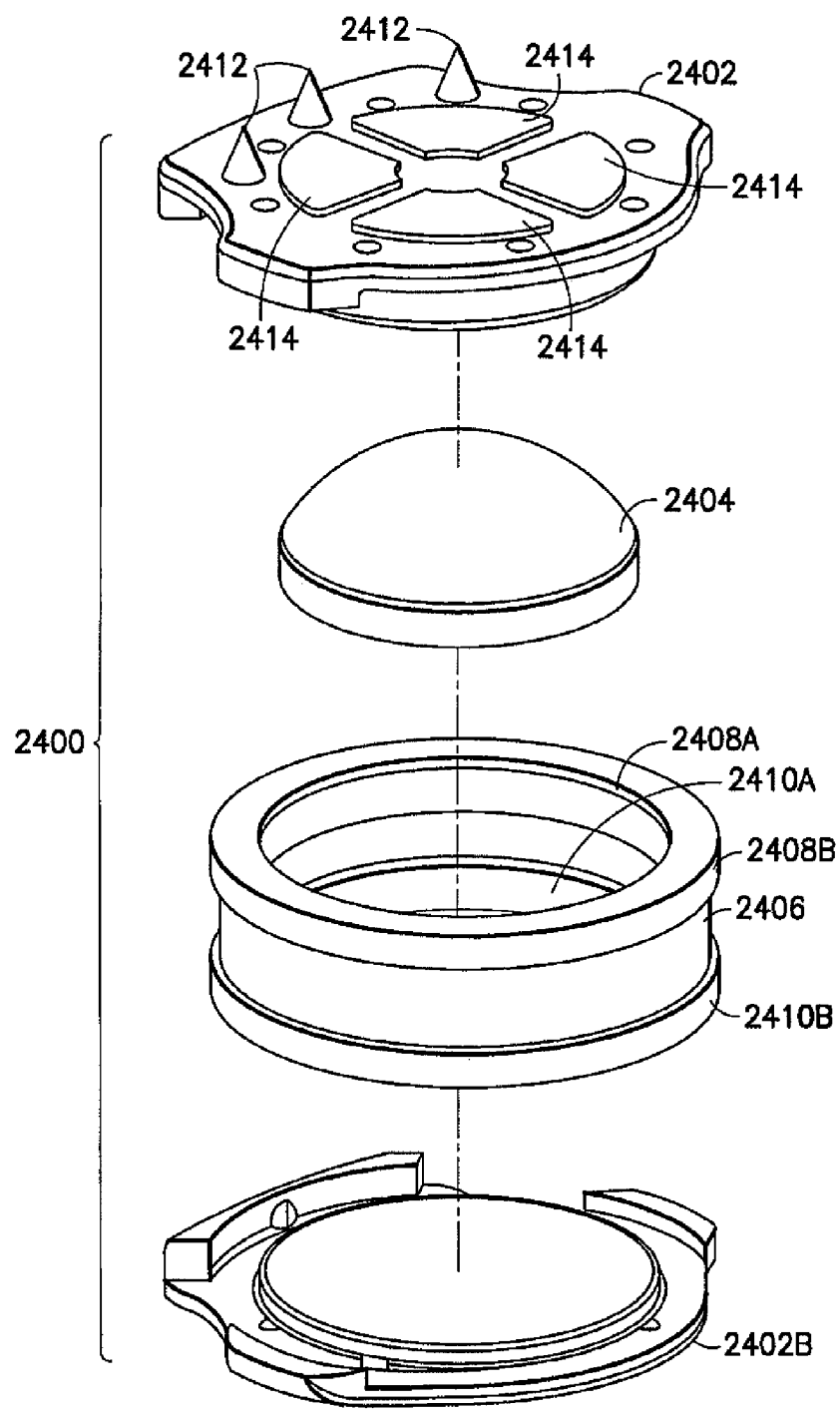
FIG. 24 shows an exploded view of an artificial intervertebral disc according to another embodiment of the present invention.
Figure 25:
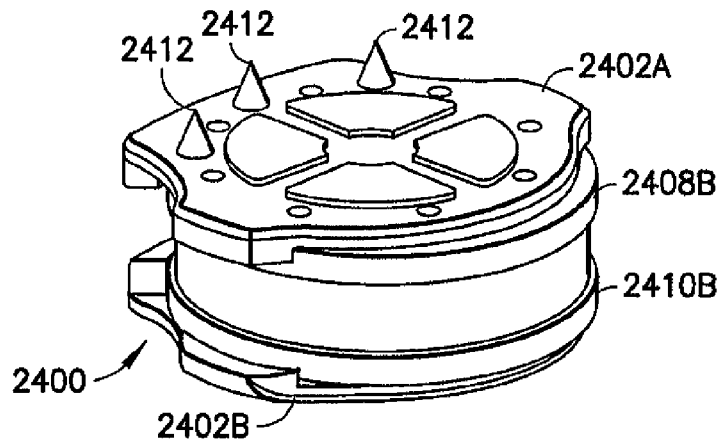
FIG. 25 shows a perspective view of the artificial intervertebral disc of FIG. 24.
Figure 26:
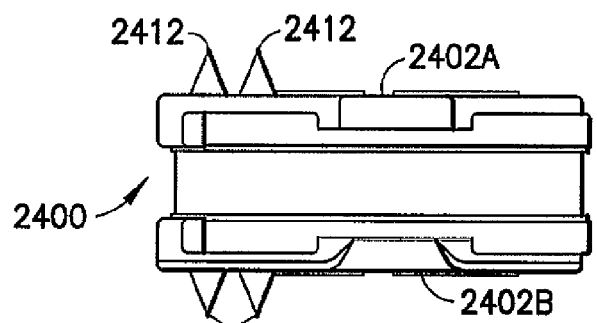
FIG. 26 shows a side view of the artificial intervertebral disc of FIG. 24.
Figure 27:
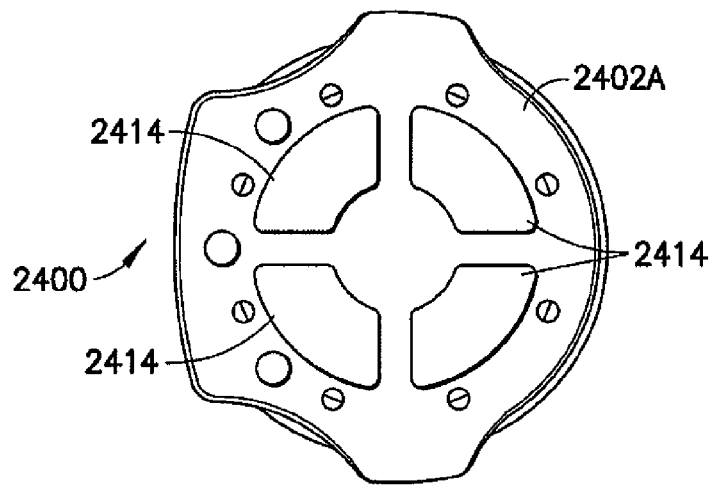
FIG. 27 shows a top view of the artificial intervertebral disc of FIG. 24.
Figure 28:
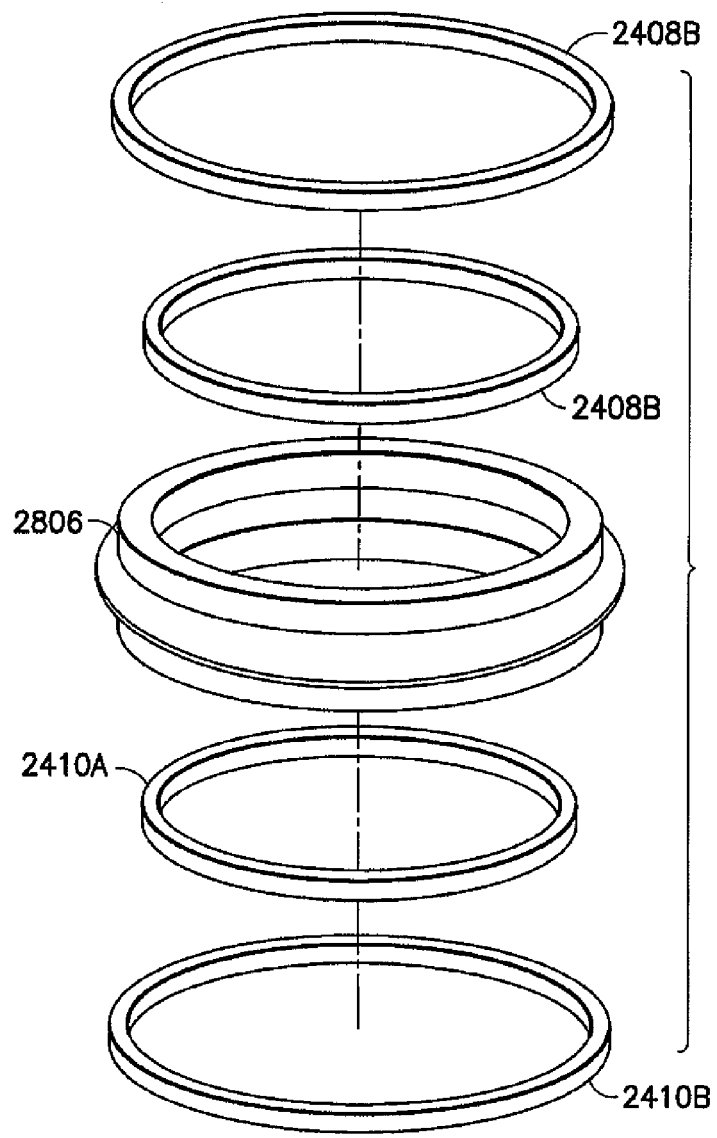
FIGS. 28-33 show additional views of components of an artificial intervertebral disc according to another embodiment of the present invention.
Figure 29:
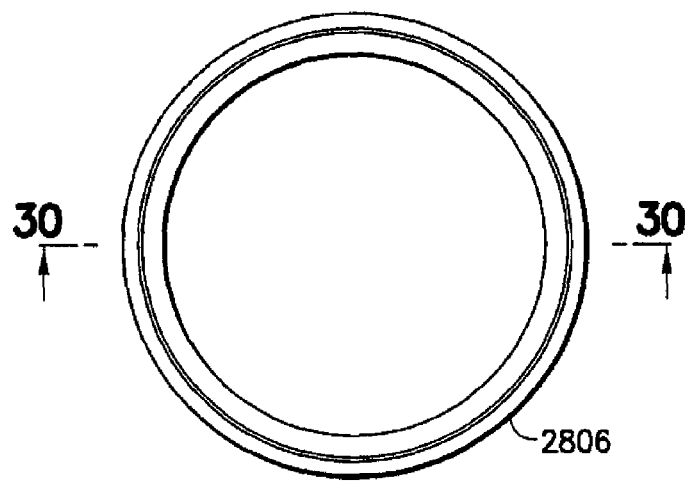
Figure 30:
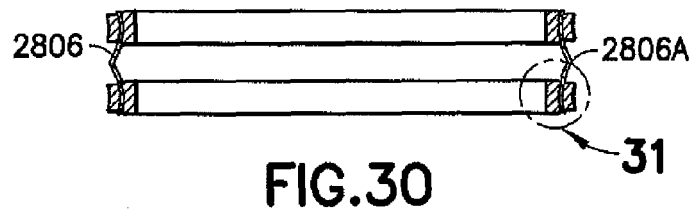
Figure 31:
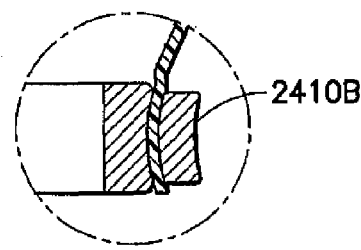

Referring now to FIGS. 23A and 23B, it is seen that Artificial Intervertebral Disc 2300 includes First Anchor Plate 2302A and Second Anchor Plate 2302B (each Anchor Plate 2302A, 2302B may comprise, for example (which example is intended to be illustrative and not restrictive), any desired biologically acceptable metal). Of note, each Anchor Plate 2302A, 2302B may have an outer surface configured to be disposed adjacent a respective vertebral endplate (not shown). Further, Core 2304 (e.g., comprising UHMPE) is sandwiched between an inner surface of Anchor Plate 2302A and an inner surface of Anchor Plate 2302B (in one example (which example is intended to be illustrative and not restrictive), the inner surfaces of Anchor Plates 2302A, 2302B may be concave for receiving therein Core 2304). In addition, Inner Column 2305 (e.g., comprising an elastomer) is also sandwiched between the inner surface of Anchor Plate 2302A and the inner surface of Anchor Plate 2302B. Moreover, Outer Column 2306 (e.g., comprising a PE (polyethelene) material, or polyester material (e.g., DACRON)) is held between First Inner Ring 2308A and First Outer Ring 2308B as well as between Second Inner Ring 2310A and Second Outer Ring 2310B for attachment to each of Anchor Plates 2302A, 2302B.

In one example (which example is intended to be illustrative and not restrictive), Outer Column 2306 is held between First Inner Ring 2308A and First Outer Ring 2308B as well as between Second Inner Ring 2310A and Second Outer Ring 2310B by crimping or rotary swaging.

In another example (which example is intended to be illustrative and not restrictive), Outer Column 2306 is held between respective inner and outer rings for attachment to each of Anchor Plates 2302A, 2302B (such as on outside vertical surfaces of Anchor Plates 2302A, 2302B) by laser welding First Inner Ring 2308A to Anchor Plate 2302A and Second Inner Ring 2310A to Anchor Plate 2302B.

Referring now to FIGS. 24-27 (showing an embodiment of the present invention), it is seen that Artificial Intervertebral Disc 2400 includes First Anchor Plate 2402A and Second Anchor Plate 2402B (each Anchor Plate 2402A, 2402B may comprise, for example (which example is intended to be illustrative and not restrictive), any desired biologically acceptable metal). Of note, each Anchor Plate 2402A, 2402B may have an outer surface configured to be disposed adjacent a respective vertebral endplate (not shown). Further, Column Filler 2404 (e.g., comprising an elastomer) is disposed between an inner surface of Anchor Plate 2402A and an inner surface of Anchor Plate 2402B (in one example (which example is intended to be illustrative and not restrictive), the inner surfaces of Anchor Plates 2402A, 2402B may be concave for receiving therein Column Filler 2404). In addition, Column 2406 (e.g., comprising a polyester (e.g., DACRON)) is held between First Inner Ring 2408A and First Outer Ring 2408B as well as between Second Inner Ring 2410A and Second Outer Ring 2410B for attachment to each of Anchor Plates 2402A, 2402B.

Still referring to FIGS. 24-27, it is noted that each of First Anchor Plate 2402A and Second Anchor Plate 2402B may include Spikes 2412 (e.g., to aid in initial fixation), Pockets 2414 (e.g., for holding a porous coating), and/or Attachment Features (e.g., to interface with one or more holding/implantation instruments).

Figure 32:
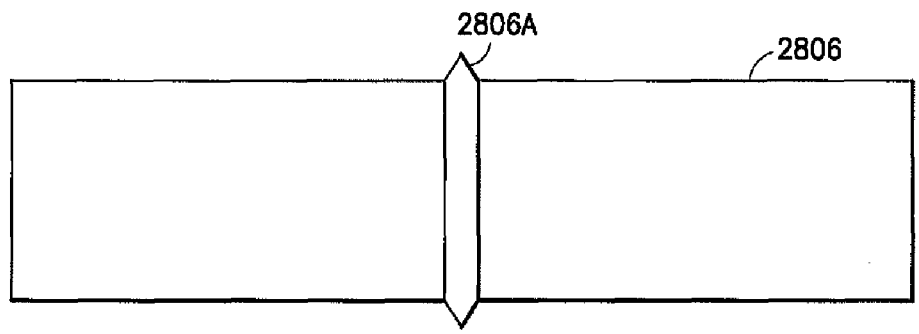
Figure 33:
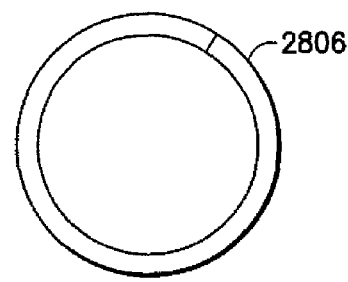
Figure 34:
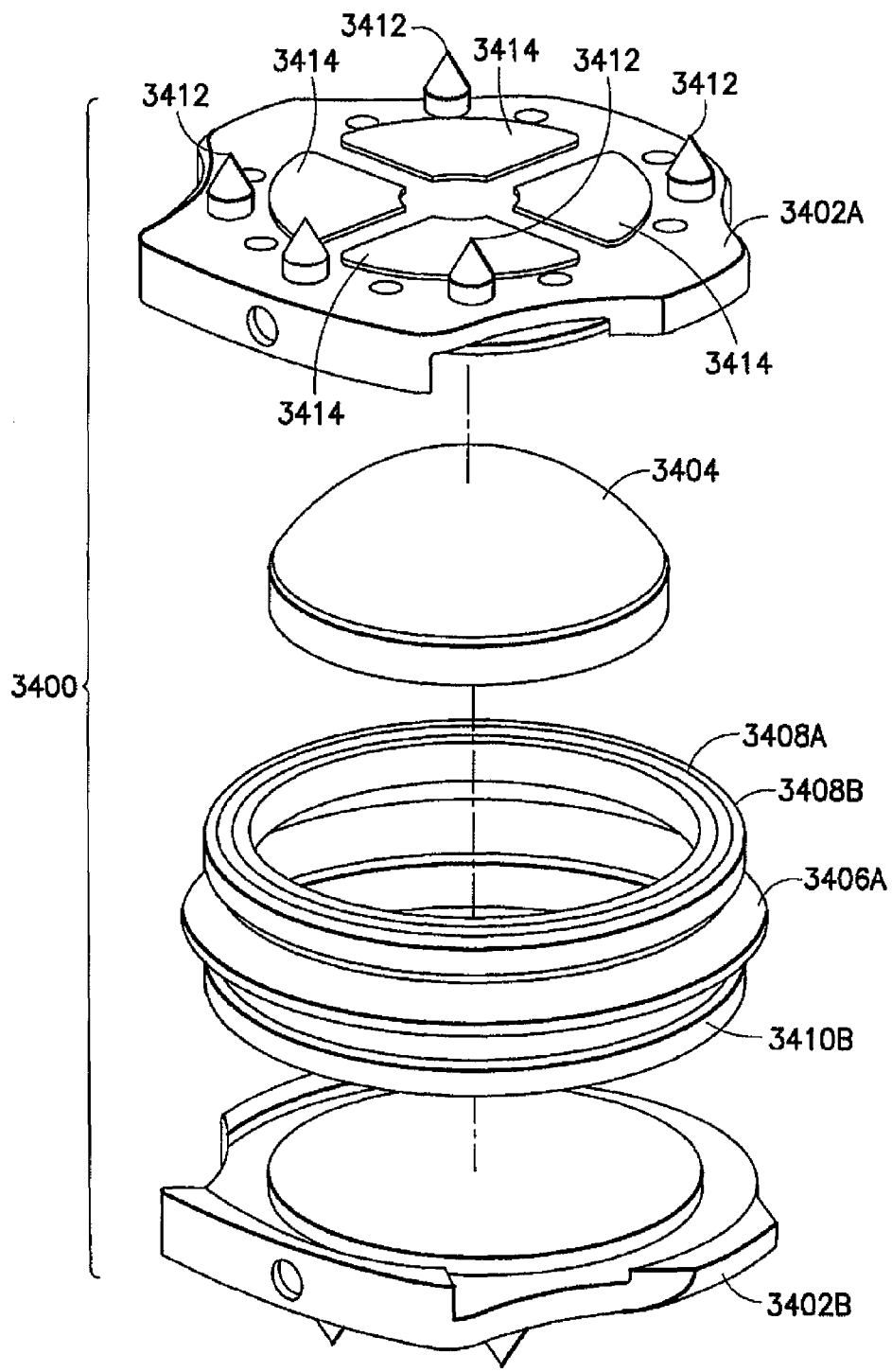
FIGS. 34-43 show additional views of components of an artificial intervertebral disc according to another embodiment of the present invention.
Figure 35:
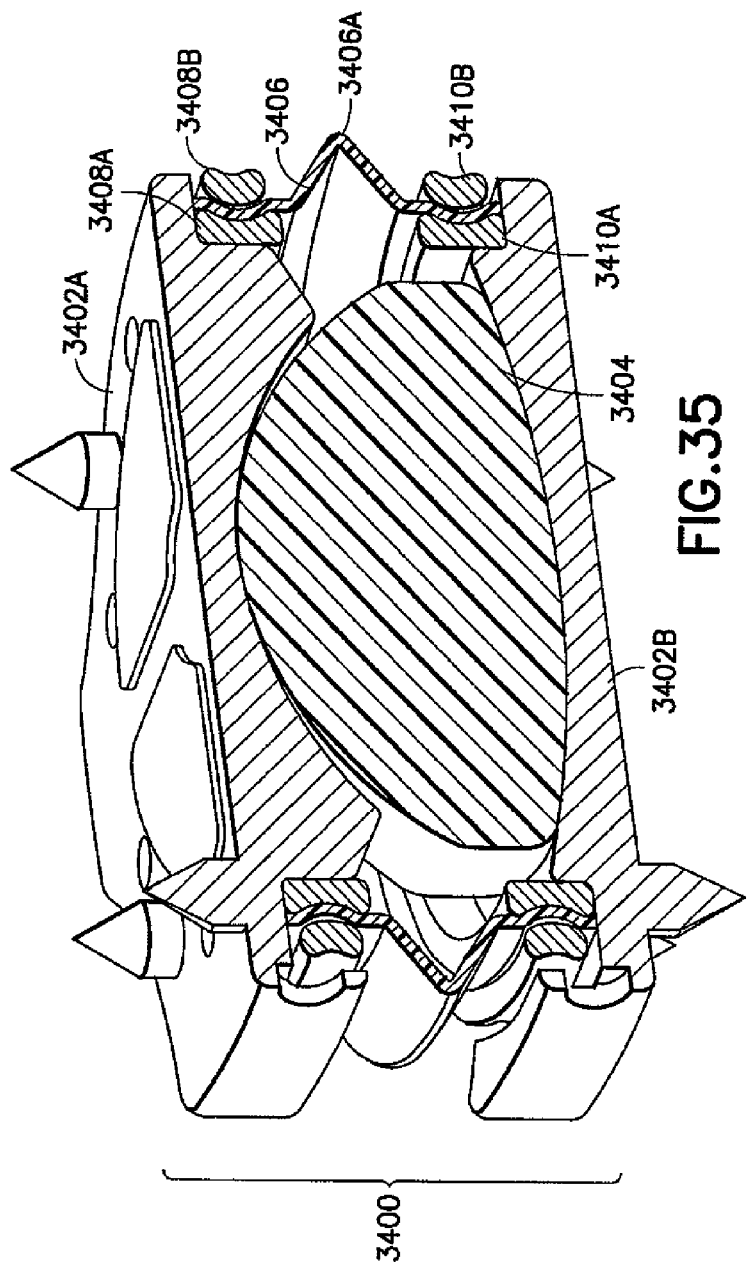
Figure 36:
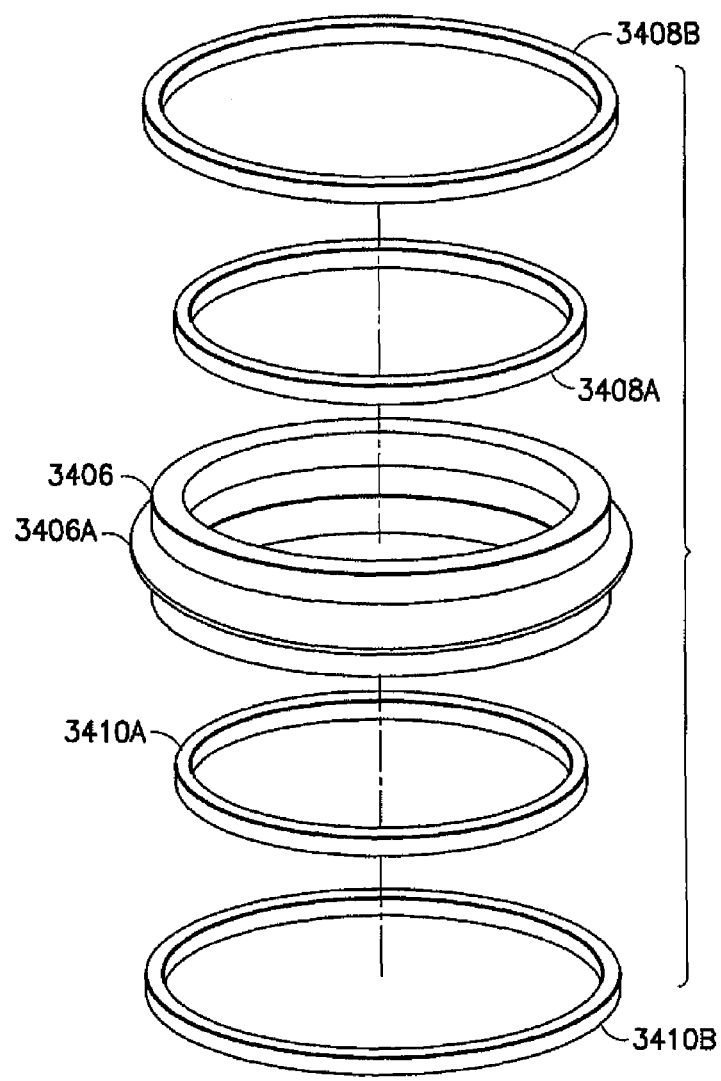
Figure 37:
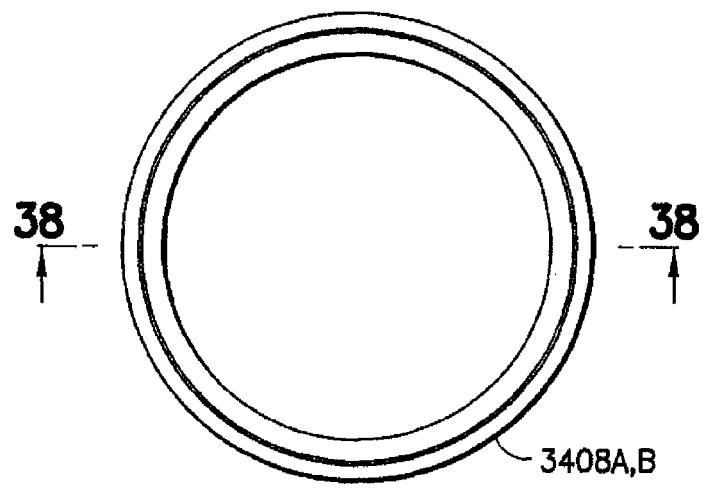
Figure 38:
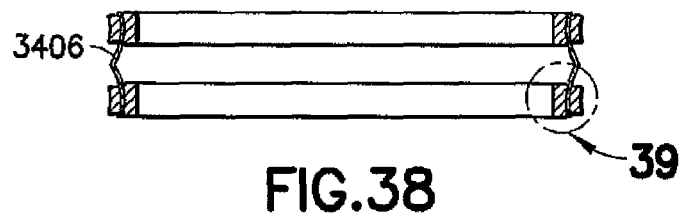
Figure 39:
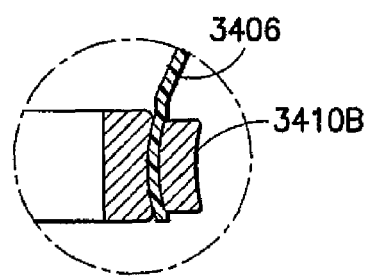
Figure 40:
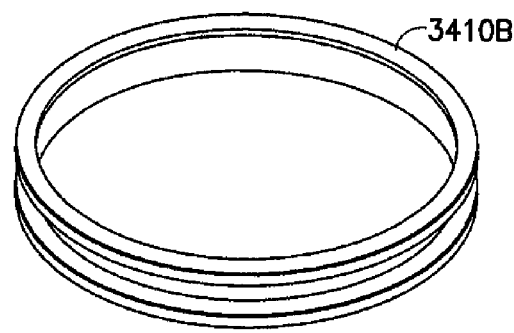
Figure 41:
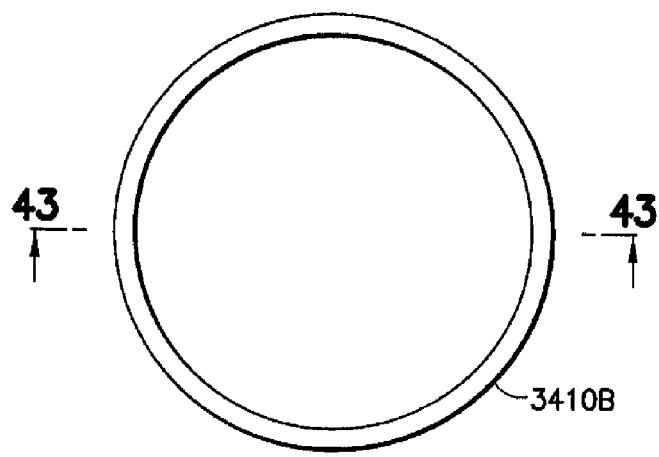
Figure 42:
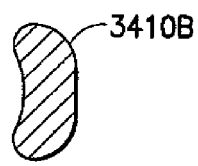
Figure 43:

Referring now to FIGS. 28-33, additional views of components of an artificial intervertebral disc according to another embodiment of the present invention are shown. Of note, the components shown in these FIGS. 28-33 are similar to those of FIGS. 24-27, with the exception that Column 2806 has therein Radial Crimp 2806A (e.g., a crimp extending around a perimeter of Column 2806). In this regard, Radial Crimp 2806A may provide flexibility which may: (a) help in assembling the AID; (b) help in implanting the AID; and/or (c) help in providing a desired deflection behavior. Of further note, FIG. 32 shows Column 2806 in an untrimmed state (thus, it is seen in this FIG. 32 has having a much longer aspect ratio than in the other Figs.).

Referring now to FIGS. 34-43 (showing an embodiment of the present invention), it is seen that Artificial Intervertebral Disc 3400 (shown in an exploded view in FIG. 34 and a cut-away view in FIG. 35) includes First Anchor Plate 3402A and Second Anchor Plate 3402B (each Anchor Plate 3402A, 3402B may comprise, for example (which example is intended to be illustrative and not restrictive), any desired biologically acceptable metal). Of note, each Anchor Plate 3402A, 3402B may have an outer surface configured to be disposed adjacent a respective vertebral endplate (not shown). Further, Column Filler 3404 (e.g., comprising an elastomer) is disposed between an inner surface of Anchor Plate 3402A and an inner surface of Anchor Plate 3402B (in one example (which example is intended to be illustrative and not restrictive), the inner surfaces of Anchor Plates 3402A, 3402B may be concave for receiving therein Column Filler 3404). In addition, Column 3406 (e.g., comprising an HTPET weave) is held between First Inner Ring 3408A and First Outer Ring 3408B as well as between Second Inner Ring 3410A and Second Outer Ring 3410B for attachment to each of Anchor Plates 3402A, 3402B.

Still referring to FIGS. 34-43, it is noted that each of First Anchor Plate 3402A and Second Anchor Plate 3402B may include Spikes 3412 (e.g., to aid in initial fixation), pockets for holding a Porous Coating 3414, and/or Attachment Features (e.g., to interface with one or more holding/implantation instruments).

As seen in these FIGS. 34-43, Column 3406 has therein Radial Crimp 3406A (e.g., a crimp extending around a perimeter of Column 3406). In this regard, Radial Crimp 3406A may provide flexibility which may: (a) help in assembling the AID; (b) help in implanting the AID; and/or (c) help in providing a desired deflection behavior.

In another embodiment the AID assembly may be constructed of first and second anchor plates, each of which has a vertebrae contacting side, and a plurality of composite structures that are fixed to the first and second anchor plates. In one example (which example is intended to be illustrative and not restrictive) 2-8 composite structures may be fixed to the anchor plates.

In another embodiment the AID assembly may be provided with one or more anchor plates that have one or more undercuts and/or one or more tabs to facilitate the anchoring of the AID assembly to the vertebral bodies. In one example (which example is intended to be illustrative and not restrictive) the tabs may be provided with screw-holes into which bone screws can be inserted to anchor the assembly to the vertebral bodies. In another example (which example is intended to be illustrative and not restrictive) the screw holes and/or the tabs may be angled relative to the vertebrae bodies (e.g., to pull all or part of the AID assembly diagonally against the vertebrae).

In another embodiment the anchor plates may be assembled such that the anchor plates are non-parallel (e.g., in order to provide a profile that substantially corresponds to the lordotic profile of the vertebral bodies/intervertebral space). In one example (which example is intended to be illustrative and not restrictive), the non-parallel angle may be about 5° to about 15°.

In another embodiment a final AID assembly may be comprised of multiple assemblies (e.g., matching left and right assemblies), each assembly having first and second anchor plates and at least one composite structure that is fixed to the anchor plates. In one example (which example is intended to be illustrative and not restrictive) the left and right assemblies may be sized and dimensioned to reside adjacent to each other when positioned in the space between vertebral bodies.

In another embodiment (e.g., related to a modular design) the column(s) of the composite structure(s) may be terminated to intermediate end-pieces, which are then affixed to the anchor plates by one or more of a variety of means, thus allowing for interchangeable heights and stiffnesses to provide a custom device for a patient's specific needs. Such customization may be provided, for example (which example is intended to be illustrative and not restrictive), via use of screw(s), threaded mechanism(s), and/or various sized insert(s) and/or ring(s).

Of note, making a portion of the column of the composite structure relatively hard (and/or connecting the column of the composite structure to a relatively hard flange or other device) may aid in attaching the column of the composite structure to the anchor plates.

Of further note, it is contemplated that each AID assembly of the present invention may be inserted using any desired surgical approach. For example (which example is intended to be illustrative and not restrictive), a posterior approach may be utilized. In another example (which example is intended to be illustrative and not restrictive), a posterior, lateral approach may be utilized. In another example (which example is intended to be illustrative and not restrictive), an anterior approach may be utilized.

In another embodiment, the AID may come in variety of 'widths'. For example (which example is intended to be illustrative and not restrictive), one AID assembly may have a "narrow" width, another AID assembly may have a "regular" width and a third AID assembly may have a "wide" width.

In another embodiment, the AID may come in variety of lengths. For example (which example is intended to be illustrative and not restrictive), one AID assembly may have a "short" length, another AID assembly may have a "regular" length and a third AID assembly may have a "tall" length.

Of note, such multiple "widths" and/or multiple "lengths" could provide the potential for the greatest amount of surface contact between the device and the vertebral endplate, thus lowering the contact stresses and reducing the potential for subsidence (gradual "sinking" of the device into the adjoining vertebral bodies).

Additionally, it is noted that during the surgical preparation of the vertebral endplate, a surgeon may scrape/score the bony surface in order to promote bone growth with the intention of securing ultimate fixation between vertebra and implant. If the scraped/scored surface is larger than the implanted device, there is a greater likelihood of bone growing up around the perimeter of the device, eventually causing bone bridging, fusing the spinal segment. A device with a surface that better matches the prepared endplate in terms of area coverage may help discourage this behavior.

In another embodiment the column may be an essentially solid chord or piece of material.

In another embodiment the column may be an essentially solid combination of materials.

In another embodiment a column could be made to have greater wall thickness on one side or end as opposed to another side or end. For example (which example is intended to be illustrative and not restrictive), the walls of the anterior side may be made thicker than the walls of the posterior side.

In another embodiment the AID assembly may be customized to provide any desired articulation, kinematic behavior, dynamic behavior and/or static properties for any given application (e.g., implantation site) and/or patient (e.g., gender, age, height, weight, activity level). For example (which examples are intended to be illustrative and not restrictive):

1. The articulation, kinematic behavior, dynamic behavior and/or static properties exhibited by the column(s) may be modified by varying the density and/or composition of the material.
2. The articulation, kinematic behavior, dynamic behavior and/or static properties exhibited by the column filler may be modified by varying the density and/or composition of the material.
3. The articulation, kinematic behavior, dynamic behavior and/or static properties exhibited by the AID assembly may be modified by varying (for individual components (e.g., column, column filler, intermediate elements, anchor plates)):
    a) column height;
    b) column width (e.g., diameter);
    c) column cross-section (shape and/or area);
    d) column wall thickness;
    e) column stiffness modulus;
    f) filler height;
    g) filler width (e.g., diameter);
    h) filler cross-section (shape and/or area);
    i) filler stiffness modulus;
    j) anchor plate material;
    k) anchor plate shape;
    l) anchor plate stiffness modulus;
    m) intermediate element material
    n) shape (e.g., curvature) of an interface between the filler and an anchor plate or intermediate element
4. The articulation, kinematic behavior, dynamic behavior and/or static properties exhibited one or more composite structures in a multiple composite structure AID assembly may be modified by varying one or more parameters discussed at paragraph 3, above, to render one or more of the composite structures stiffer than one or more of the other composite structures in order to add stiffness locally and to aid in mimicry of in vivo non-homogeneous stiffness topography (e.g., the in vivo topography relating to the area of relatively higher stiffness in the posterior region of the vertebral body versus the relatively lower stiffness in the anterior region of the vertebral body).
5. In the context of a multiple composite structure AID assembly, one or more of the composite structures may be positioned appropriately between the anchor plates as follows:
    a) one or more composite structures may be placed an increased distance from the center of the implant (e.g., to aid in increasing torsional stiffness of the implant);
    b) lateral positioning of one or more composite structures may be used (e.g., to aid in controlling lateral bending stiffness of the implant); and/or
    c) fore/aft positioning of one or more composite structures may be used (e.g., to aid in controlling flexion/extension stiffness of the implant).
6. In the context of a multiple composite structure AID assembly, any desired number of composite structures may be utilized.
7. In the context of a multiple hole composite structure, the articulation, kinematic behavior, dynamic behavior and/or static properties exhibited may be controlled in a similar manner as discussed at paragraphs 4-6, above, with regard to the multiple composite structure AID (e.g., the spacing between the holes may be varied, the size/cross-sectional area/cross-sectional shape of the holes may be varied, the position of the various holes may be varied, the number of holes may be varied etc.).

In another example (which example is intended to be illustrative and not restrictive), the composite structure may be configured such that the composite structure has associated therewith, in at least one axis, a load versus deflection behavior substantially similar to that of a substantially healthy human intervertebral disc.

In another example (which example is intended to be illustrative and not restrictive), the load versus deflection behavior may be selected from the group including (but not limited to): (a) dynamic behavior, which dynamic behavior is a function of a time rate application of load; (b) kinematic behavior; and (c) static behavior.

In another example (which example is intended to be illustrative and not restrictive), the load versus deflection behavior may include a non-linear relationship between an amount of force required to compress the composite structure and a deflection of the composite structure.

In another example (which example is intended to be illustrative and not restrictive), a stiffness of the composite structure may increase as the composite structure is compressed.

In another example (which example is intended to be illustrative and not restrictive), the elastomer may be selected from the group including (but not limited to): (a) a silicone; (b) a urethane; and (c) a thermoplastic elastomer In another example (which example is intended to be illustrative and not restrictive), the column may be impregnated with a material that aids in preventing at least one of (but not limited to): (a) biological ingrowth into the column; and (b) biological attachment to the column.

In another example (which example is intended to be illustrative and not restrictive), the column may be coated with a material that aids in preventing at least one of (but not limited to): (a) biological ingrowth into the column; and (b) biological attachment to the column.

In another example (which example is intended to be illustrative and not restrictive), the artificial intervertebral disc may be configured to be implanted by at least one method selected from the group including (but not limited to): (a) posterior implantation; and (b) anterior implantation.

In another embodiment the column and/or the column filler may contain a compression element (e.g., a spring (e.g., constructed of a biocompatible material, such as titanium)).

Of note, the materials used in constructing the AID assembly may be strong, durable and biocompatible. For example (which example is intended to be illustrative and not restrictive), the anchor plates may be constructed of titanium 6AL4V ELI (extra low interstitial), a titanium alloy containing 6% aluminum and 4% vanadium. Any elastomeric or non-elastomeric materials utilized in the assembly may be biocompatible. One of ordinary skill in the art would readily appreciate the other materials that could be used to construct implants according to the present invention.

As mentioned above, the column(s) may be coated (e.g., to help prohibit the growth of tissue and/or bone on the column(s). In one example (which example is intended to be illustrative and not restrictive), the coating may be silicone, urethane, any desired biocompatible elastomer layer and/or any combination thereof.

In another embodiment the column(s) may be impregnated with the filler (e.g., the elastomer).

In another embodiment the device may resist shear translation and flexion of the spine and may produce shear at one or more adjacent joints (e.g., a superior adjacent joint).

In another embodiment flexion/extension may produce shear translation and rotation of a superior vertebral body.

In another embodiment one or more of the anchor member surfaces may be shaped to substantially match adjacent vertebral endplate surfaces to allow for minimal "carpentry" (or bone removal/shaping) during surgery to achieve good contact area (e.g. in cervical spine, the cephalad (towards the head) surface of the implant may be convex in the A-P (anterior-posterior) direction to match the A-P concavity in the vertebral endplate on the caudad (towards the feet) end of the vertebral body cephalad to the disc space and the caudad surface of the implant may be convex laterally to match the lateral concavity in the vertebral endplate on the cephalad end of the vertebral body caudal to the disc space).

In another embodiment one or more pieces of the AID may be sterilized separately, or a final AID unit may be sterilized as a unit. In one specific example (which example is intended to be illustrative and not restrictive), a final AID unit may be placed in a pouch and then sterilized (through the pouch).

Various structural features of the invention, and methods for installing an AID assembly, and for stabilizing the AID assembly, have been described. In this regard, it is believed that when the AID assembly of the present invention is inserted between vertebral bodies and subjected to customary loads, the AID assembly may perform similar to the way in which a healthy intervertebral disc would perform. Of note, the implants of the present invention may provide one or more of the following attributes when inserted in the body (e.g., between vertebrae):

Essentially the same articulation as a healthy intervertebral disc (e.g., intervertebral lumbar disc, intervertebral cervical disc, intervertebral thoracic disc) may be realized;

Essentially the same kinematic behavior as a healthy intervertebral disc (e.g., intervertebral lumbar disc, intervertebral cervical disc, intervertebral thoracic disc) may be realized;

Essentially the same dynamic behavior as a healthy intervertebral disc (e.g., intervertebral lumbar disc, intervertebral cervical disc, intervertebral thoracic disc) may be realized;

The static properties of the implant and a healthy intervertebral disc (e.g., intervertebral lumbar disc, intervertebral cervical disc, intervertebral thoracic disc) may be substantially identical;

The implant may be biocompatible;

The device may be implanted by posterior and/or anterior approaches;

The device may install in a relatively short period of time (e.g., around 90 minutes);

The device may exhibit positive results in fatigue tests (e.g., the device may be usable after $10 \times 10^6$ cycles);

The device may survive static loading, shear loading and testing to induce expulsion;

The device may fixate relatively rapidly to vertebral bodies;

The device may minimize contact stress with vertebral bodies at the device interface; and The device may be auto-clavable.

In other embodiments the AID assembly may include one or more of the following features:

The device may have lordosis (lordotic angle) built in (in one example the lordotic angle may place the composite structure substantially coincident with the axis of the functional spinal unit ("FSU"))

The anchor plate(s) may have surface treatment(s) to encourage osseointegration (bony ingrowth) to establish ultimate fixation to vertebral endplates. Such surface treatments may include (but not be limited to): electro-chemical etch; plasma-sprayed Ti; sintered metallic beads or shards; bioactive/osseoinductive/osseoconductive ceramic coating (e.g., hydroxyapatite (HA))

The device may employ no screws, a single screw or multiple screws for fixation

The device may include features to establish immediate fixation to vertebral endplates. Such features may include (but not be limited to): screw(s); keel(s); serration(s) (e.g., backward-facing serrations or angled bosses to 'bite' into place); sharp protrusion(s); finger(s)/protrusion(s) that can be deployed once device is in place The device may dampen strain energy via compliant composite structure(s)

The columns may be reinforced. Such reinforcement may include (but not be limited to): exterior reinforcement; interior reinforcement; circumferential rib(s)/band(s); spiral ribbing/banding; rib(s)/band(s) of nitinol, metal; rib(s)/band(s) disconnected from column; rib(s)/band(s) connected to column; fusion weld; as part of extrusion process A connection between a column and an anchor plate may include a frictional component, for example, due to compressive force capturing column/flange to plate (friction may be enhanced by roughened surface geometry (e.g., on mating anchor plate surface))

A capturing component may be welded to an anchor plate

Holes in an anchor plate may enhance ability of sterilization (e.g., with EtO gas)

The column may be designed such that when the AID assembly is in neutral condition (e.g., not flexed or twisted) the column (e.g., the DACRON) is somewhere in the middle of its elongation ratio (not fully compressed or elongated).

The column surrounding the column filler may constrain the radial bulge of the column filler during compression, causing the load-deflection response of the composite structure to be non-linear, like a healthy disc A bi-concave core may ride on convex dome surfaces such that the core follows the motion of the 'leading' anchor plate, promoting motion that mimics the shear displacement in an intact disc during bending The AID assembly may have multiple height options to appropriately match the height of disc being replaced and allowing for appropriate distraction to the segment during and after surgery to decompress anatomy, e.g. foraminal nerves (addressing the pathology)

The AID assembly may have multiple sizes (e.g., in the anterior-posterior (A-P) dimension), allowing for proper placement of the composite structure coincident with the axis of the FSU In another embodiment the column of the composite structure may be affixed to the anchor plates to form a structural unit (this is, the column forms a structural "bridging link" between the anchor plates).

In another embodiment the AID assembly is not pre-stressed. Since the AID assembly of this embodiment is not pre-stressed, the column filler (e.g., elastomer) will not exhibit any significant amount of "creep". In addition, the AID assembly of this embodiment will, at times, be under essentially no stress (e.g., when the patient using the AID assembly is lying down). Of note, this is similar behavior to a natural disc.

Of note, when a column is utilized without a column filler (e.g., in the form of an essentially homogeneous structure), such a column may be integrated into the AID assembly (e.g., in terms of attachment to the anchor plates, patient customization) in essentially the same manner as a composite structure discussed herein.

In another example (which example is intended to be illustrative and not restrictive), the surgeon may (during the surgical procedure) make the requisite incisions or access the site where the unhealthy or damaged disc is to be removed. After removal of the unhealthy or damaged disc or the unhealthy or damaged portion(s) of the disc, the surgeon may cut grooves in the endplates of the vertebral bodies that were adjacent to the removed disc. The grooves that are cut may be sized and shaped to correspond to an interface on an elevated portion of the anchor plate(s). Of note, the surgical procedure may also involve removing healthy portion(s) of the patient's disc(s) to the extent required for implantation of the AID assembly.

In one embodiment the compressibility of the implant of the present invention may prove helpful during the implanting procedure. For example, (which example is intended to be illustrative and not restrictive), as the implant is being inserted between the vertebrae, the implant may be compressed to smaller proportions than its uncompressed height. The surgeon can then, prior to releasing the implant from its compressed height, adjust its position to insure that the elevated interface on the anchor plates and the grooves cut into the vertebral bodies are aligned with each other. After the surgeon has ensured this is the case, the implant may be released from its compressed state (e.g., so that the elevated interface enters the grooves)

Alternatively, the grooves may be cut in the vertebral body with a matching undercut, such that the anchor plates may be inserted (e.g., from the side, front or back) in a dovetail configuration. This embodiment may allow for positive initial tensile attachment between the anchor plates and the endplates, without having to wait for bony ingrowth.

While a number of embodiments of the present invention have been described, it is understood that these embodiments are illustrative only, and not restrictive, and that many modifications may become apparent to those of ordinary skill in the art. For example, one or more components may be constructed of Ti, cobalt chromium, surgical steel and/or any combination thereof. Further, customization may be carried out using multiple, interchangeable components (e.g., interchangeable composite structures). Further still, the customization may be carried out using a family of standard parts. Further still, customization of the AID assembly may be done at the place of manufacture (e.g., by a technician at the factory) and/or at the place of implantation (e.g., by a surgeon at the hospital). Further still, the vertebra contacting side of the anchor members (i.e., the side of the anchor members facing the "upper" and "lower" faces of the vertebrae) may include gripping, tissue ingrowth promoting and/or bone ingrowth promoting elements, such as, for example (which examples are intended to be illustrative and not restrictive), grooves, teeth, protrusions, depressions or any combination thereof. Further still, mounting tabs associated with the anchor members (which mounting tabs may contact the vertebrae on the generally vertical "outer" faces thereof) may interface with the vertebrae along a planar interface, a curved interface, or a combination thereof. Further still, the mounting tabs may include gripping, tissue ingrowth promoting and/or bone ingrowth promoting elements such as described above. Further still, the column filler (e.g., elastomer) within the column may be of sufficient hardness as to form a distinct "core" within the column (such that the core fills essentially the entire space within the column or the core fills less than the entire space within the column (e.g., having one or more voids above the core, below the core and/or around the core between the core and the column)). Further still, the column filler (e.g., elastomer) within the column may be of insufficient hardness as to form a distinct "core" within the column but may instead fill the column in a more or less "fluid" manner (such that the column filler fills essentially the entire space within the column or the column filler fills less than the entire space within the column (e.g., having one or more voids above the column filler, below the column filler and/or around the column filler between the core and the column). Further still, the column filler (e.g., elastomer) may be extruded/injected onto the column(s). Further still, the column filler (e.g., elastomer) may protrude out from the top, bottom and/or side(s) of the column. Further still, the protruding column filler (e.g., elastomer) may be used to aid in attachment of the composite structure to the anchor plate (e.g., the protruding elastomer may be attached directly or indirectly (via an intermediate element) to an anchor plate using any desired attachment mechanism). Further still, the column may comprise any desired fiber and/or fabric. Further still, the attachment of the column(s) and/or composite structure(s) to the anchor plates may be carried out using a press fit, a rotary swage, welding (e.g., spot or continuous), a number of discrete interference dings, a forced interference fit, a threaded fit, a punch mechanism at a seam between parts and/or any other desired method (as well, of course, as any combination thereof). Further still, the device may be shaped as desired, such as having a circular shape, an oval shape or a kidney shape, for example (this could be effected by providing a desired shape to any of the components (e.g., the anchor plates and/or the column(s) and/or the composite structure(s))). Further still, the composite structure(s) may essentially fill the space between the anchor plates or there may be empty space between the composite structure(s). Further still, the column filler, the material used to coat the column(s) and/or the material impregnated into the column(s) may be any desired compressible, elastic compressible, extrudable and/or flowable material (or combination thereof). Further still, the load/deflection curves associated with the present invention may result from underlying data having applied thereto any desired type of curve fitting (e.g., polynomial curve fitting to the second or third power). Further still, all dimensions, engineering notes, specifications, etc. identified in the Figs. are intended to be examples and not be restrictive. Further still, any desired number of crimps may fully and/or partially encircle the perimeter of the column. Further still, any steps may be carried out in any desired order (and certain steps may be omitted and/or other steps added).

What is claimed is:

1. An artificial intervertebral disc, comprising:
   a column comprising a first polymeric material;
   a column filler comprising a second polymeric material;
   a first crimped-ring set comprising a first inner ring and a first outer ring, the first crimped-ring set being disposed adjacent a first end of the column, and at least a portion of the column being held between the first inner ring and the first outer ring;
   a second crimped-ring set comprising a second inner ring and a second outer ring, the second crimped-ring set being disposed adjacent a second end of the column, and at least a portion of the column being held between the second inner ring and the second outer ring;
   a first anchor member; and
   a second anchor member, wherein
   at least one of the first inner ring and the first outer ring of the first crimped-ring set provides a mechanism to attach the column to the first anchor member, and
   at least one of the second inner ring and the second outer ring of the second crimped-ring set provides a mechanism to attach the column to the second anchor member.

2. The artificial intervertebral disc of claim 1, wherein the first polymeric material is DACRON.

3. The artificial intervertebral disc of claim 1, wherein
   at least one of the first inner ring and the first outer ring of the first crimped-ring set provides a mechanism to attach the first end of the column to the first anchor member, and
   at least one of the second inner ring and the second outer ring of the second crimped-ring set provides a mechanism to attach the second end of the column to the second anchor member.

4. The artificial intervertebral disc of claim 3, wherein
   at least the first inner ring of the first crimped-ring set is in contact with the first anchor member, and
   at least the second inner ring of the second crimped-ring set is in contact with the second anchor member.

5. The artificial intervertebral disc of claim 4, wherein the contact between the first inner ring of the first crimped-ring set and the first anchor member comprises an interference fit, and
   the contact between the second inner ring of the second crimped-ring set and the second anchor member comprises an interference fit.

6. The artificial intervertebral disc of claim 1, wherein a face of the first inner ring and a face of the first outer ring between which the column is held are complementary to one another.

7. The artificial intervertebral disc of claim 6, wherein one of the complementary faces comprises a concave portion and the other of the complementary faces comprises a convex portion.

8. The artificial intervertebral disc of claim 7, wherein the complementary face of the first inner ring comprises a concave portion and the complementary face of the first outer ring comprises a convex portion.

9. The artificial intervertebral disc of claim 1, wherein a face of the second inner ring and a face of the second outer ring between which the column is held are complementary to one another.

10. The artificial intervertebral disc of claim 9, wherein one of the complementary faces comprises a concave portion and the other of the complementary faces comprises a convex portion.

11. The artificial intervertebral disc of claim 10, wherein the complementary face of the second inner ring comprises a concave portion and the complementary face of the second outer ring comprises a convex portion.

12. The artificial intervertebral disc of claim 1, wherein the column includes at least one crimp around at least a portion of a perimeter of the column.

13. The artificial intervertebral disc of claim 12, wherein the crimp is around the entire perimeter of the column.

14. The artificial intervertebral disc of claim 12, wherein the crimp provides added flexibility to the column.

15. The artificial intervertebral disc of claim 14, wherein the added flexibility permits a first portion of the column on one side of the crimp to bend away from a second portion of the column on the other side of the crimp.

16. The artificial intervertebral disc of claim 12, wherein the crimp is at a position essentially equidistant from each of the first anchor member and second anchor member.

17. The artificial intervertebral disc of claim 1, wherein the column has a hole therethrough.

18. The artificial intervertebral disc of claim 17, wherein at least one of the column and the hole in the column has a substantially circular cross-section.

19. The artificial intervertebral disc of claim 18, wherein each of the column and the hole in the column has a substantially circular cross-section.

20. The artificial intervertebral disc of claim 19, wherein the column filler is disposed within the hole in the column.

21. The artificial intervertebral disc of claim 20, wherein the column filler is selected from the group consisting of: a silicone, a urethane, and a thermoplastic elastomer.

22. The artificial intervertebral disc of claim 1, wherein at least one of the first anchor member and the second anchor member has a porous region that permits tissue in growth.

23. The artificial intervertebral disc of claim 22, wherein each of the first anchor member and the second anchor member has a porous region that permits tissue in growth.

24. The artificial intervertebral disc of claim 1, wherein at least one of the first anchor member and the second anchor member has at least one protrusion that grips a respective vertebral body endplate.

25. The artificial intervertebral disc of claim 24, wherein each of the first anchor member and the second anchor member has at least one protrusion that grips a respective vertebral body endplate.

26. The artificial intervertebral disc of claim 24, wherein the protrusion is a conically-shaped spike.

27. The artificial intervertebral disc of claim 1, wherein the artificial intervertebral disc is configured to be implanted by at least one method selected from the group consisting of: posterior implantation and anterior implantation.

28. The artificial intervertebral disc of claim 1, wherein the first anchor member comprises an edge portion extending beyond a side of the column, thereby preventing the column from sliding past a side of the edge portion of the first anchor member.

29. The artificial intervertebral disc of claim 28, wherein the first anchor member comprising the edge portion extending beyond the side of the column prevents the column from sliding past an outer side of the edge portion of the first anchor member.

30. The artificial intervertebral disc of claim 1, wherein the first inner ring is distinct from the first anchor member.

31. The artificial intervertebral disc of claim 1, where in the first crimped-ring set is distinct from the second crimped-ring set.

\* \* \* \* \*